US008287886B2

(12) United States Patent
Montanes et al.

(10) Patent No.: US 8,287,886 B2
(45) Date of Patent: Oct. 16, 2012

(54) TUBERCULOSIS VACCINE

(75) Inventors: Carlos Martin Montanes, Saragossa (ES); Brigitte Gicquel, Saragossa (ES); Esther Perez Herran, Saragossa (ES); Jesus Gonzalo Asensio, Saragossa (ES); Ainhoa Arbues Arribas, Saragossa (ES)

(73) Assignee: Universidad de Zaragoza, Saragossa (ES)

( * ) Notice: Subject to any disclaimer, the term of this patent is extended or adjusted under 35 U.S.C. 154(b) by 132 days.

(21) Appl. No.: 12/294,199

(22) PCT Filed: Mar. 14, 2007

(86) PCT No.: PCT/ES2007/070051
§ 371 (c)(1),
(2), (4) Date: Jan. 11, 2010

(87) PCT Pub. No.: WO2007/110462
PCT Pub. Date: Oct. 4, 2007

(65) Prior Publication Data
US 2010/0129407 A1    May 27, 2010

(30) Foreign Application Priority Data

Mar. 24, 2006 (ES) .................................. 200600761

(51) Int. Cl.
*A61K 39/04* (2006.01)
*A61K 45/00* (2006.01)
*A61K 49/00* (2006.01)
(52) U.S. Cl. .... 424/248.1; 424/9.2; 424/9.1; 424/184.1; 424/234.1; 424/278.1; 424/93.2; 424/93.4; 435/243; 435/440; 435/320.1
(58) Field of Classification Search .................. 424/9.1, 424/9.2, 184.1, 234.1, 248.1, 278.1, 93.2, 424/93.4; 435/243, 440, 320.1
See application file for complete search history.

(56) References Cited

U.S. PATENT DOCUMENTS 7,468,190 B2   12/2008 Montaines et al.

FOREIGN PATENT DOCUMENTS

WO    WO 03/012075 A1    2/2003

OTHER PUBLICATIONS

Cole, S.T. et al. Nature, vol. 393, pp. 537-544, 1998.*
Esther Perez, et al., "An Essential role for *phoP* in *Mycobacterium tuberculosis* virulance", Molecular Microbiology, 2001, pp. 179-187, vol. 41, No. 1.
Luis Reinaldo Camacho, et al., "Identification of a Virulence Gene Cluster of *Mycobacterium tuberculosis* by Signature-Tagged Transposon Mutagenesis", Molecular Microbiology, 1999, pp. 257-267, vol. 34, No. 2.
Carlos Martin, et al., "The live *Mycobacterium tuberculosis phoP* Mutant Strain is More Attenuated than BCG and Confers Protective Immunity Against Tuberculosis in Mice and Guinea Pigs", Vaccine, Apr. 2006, pp. 3408-3419, vol. 24, No. 17.
E. Infante, et al., "Immunogenicity and Protective Efficacy of the *Mycobacterium tuberculosis fadD26 mutant*", Clinical and Experimental Immunology, 2005, pp. 21-28, vol. 141, No. 1.
Shaun B. Walters, et al., "The *Mycobacterium tuberculosis* PhoPR Two-Component System Regulates Genes Essential for Virulence and Complex Lipid Biosynthesis", Molecular Microbiology, Apr. 2006, pp. 312-330, vol. 60, No. 2.
Jesus Gonzalo Asensio, et al., "The Virulence-Associated Two-Component PhoP-PhoR System Controls the Biosynthesis of Polyketide-derived Lipids in *Mycobacterium tuberculosis*", Journal of Biological Chemistry, Jan. 20, 2006, pp. 1313-1316, vol. 281, No. 3.
Luis R. Camacho, et al., "Analysis of the Phthiocerol Dimycocerosate Locus of *Mycobacterium tuberculosis*. Evidence at this Lipid is Involved in the Cell Wall Permeability Barrier", Journal Biological Chemistry, 2001, pp. 19845-19854, vol. 276, No. 23.
International Search Report dated Jul. 16, 2007 (Four (4) pages).
T. Imaeda, "Deoxyribonucleic Acid Relatedness Among Selected Strains of *Mycobacterium tuberculosis*, *Mycobacterium bovis*, *Mycobacterium bovis*, BCG, *Mycobacterium microti*, and *Mycobacterium africanum*", International Journal of Systematic Bacteriology, Apr. 1985, vol. 35, No. 2, pp. 147-150.
Dick van Soolingen et al., "A Novel Pathogenic Taxon of the *Mycobacterium tuberculosis* Complex, Canetti: Characterization of an Exceptional Isolate from Africa", International Journal of Systematic Bacteriology, Oct. 1997, vol. 47, No. 4, pp. 1236-1245.

* cited by examiner

*Primary Examiner* — Rodney P. Swartz
(74) *Attorney, Agent, or Firm* — Crowell & Moring LLP

(57) ABSTRACT

An isolated microorganism belonging to the genus *Mycobacterium*, having one or both of an inactivated gene Rv0757 that confers a PhoP– phenotype and an inactivated second gene which prevents the production of DIM (DIM– phenotype). Methods of making the microorganism, related pharmaceutical formulations and vaccines are also provided, as are related methods of treatment and vaccination. The pharmaceutical formulation may also serve as a vector or adjuvant.

14 Claims, 16 Drawing Sheets

Lung

Spleen

Figure 1:
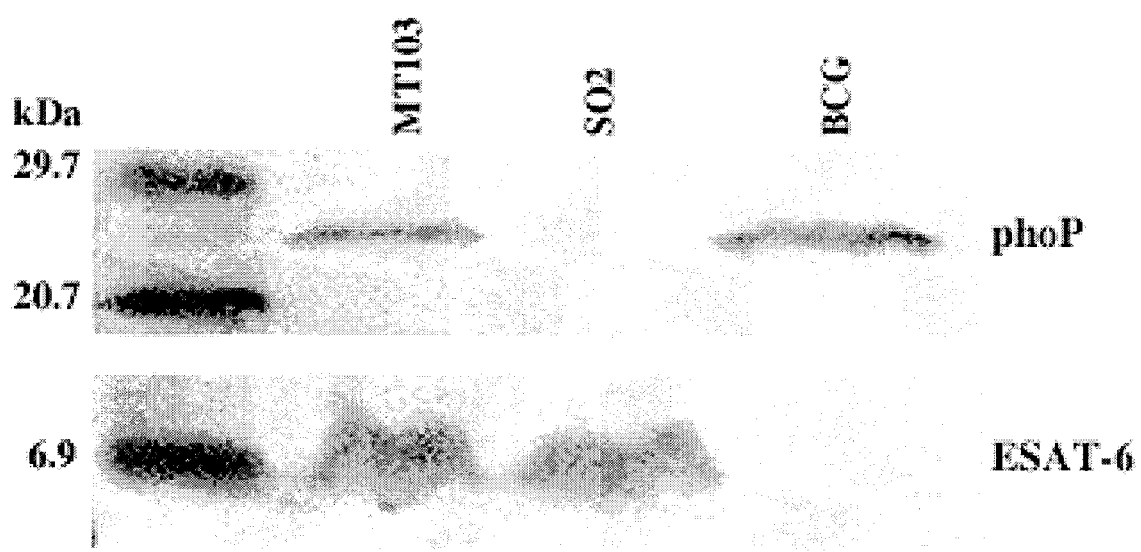

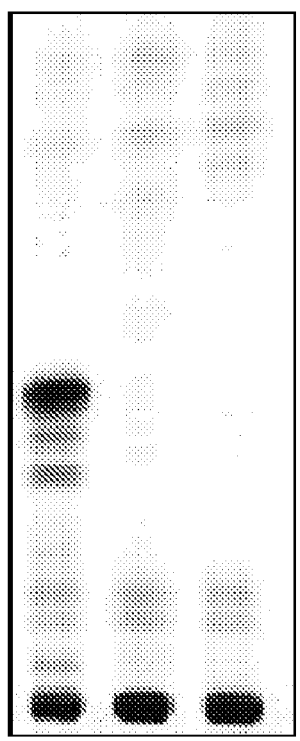 
Fig. 8a
Fig. 8b

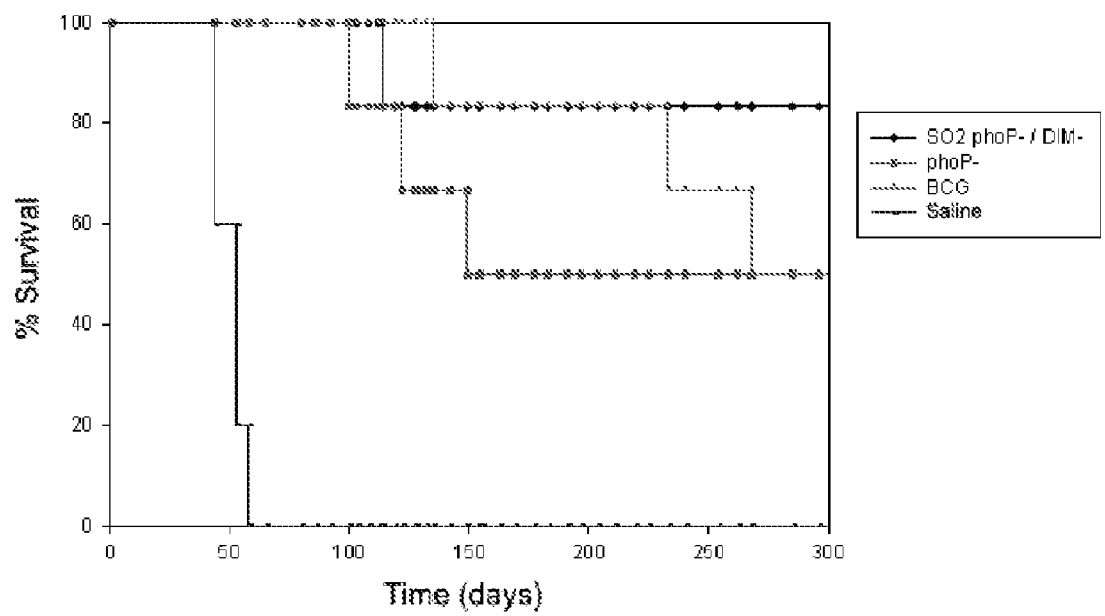
Fig. 13
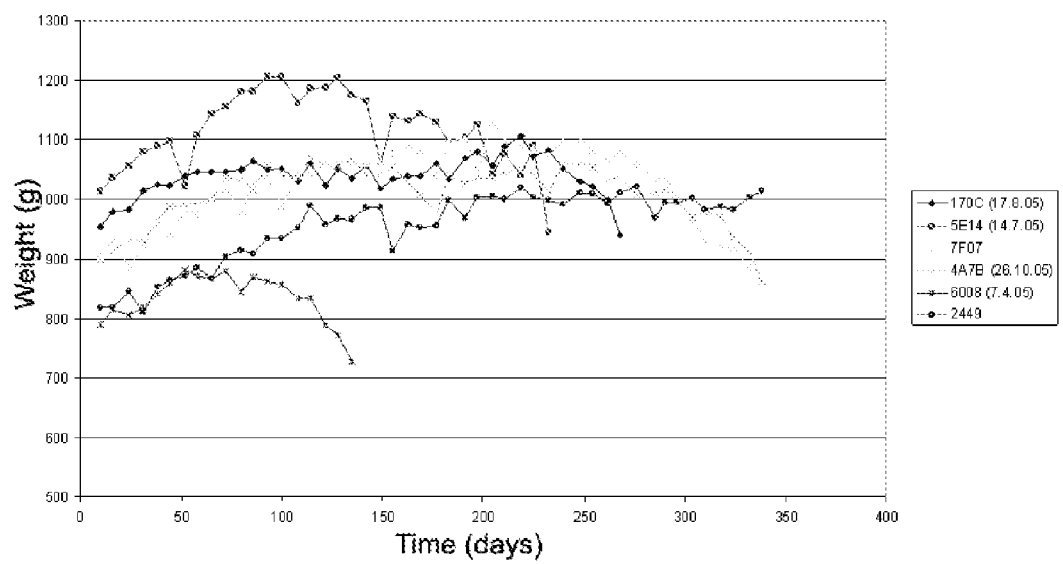
Fig. 14a₁

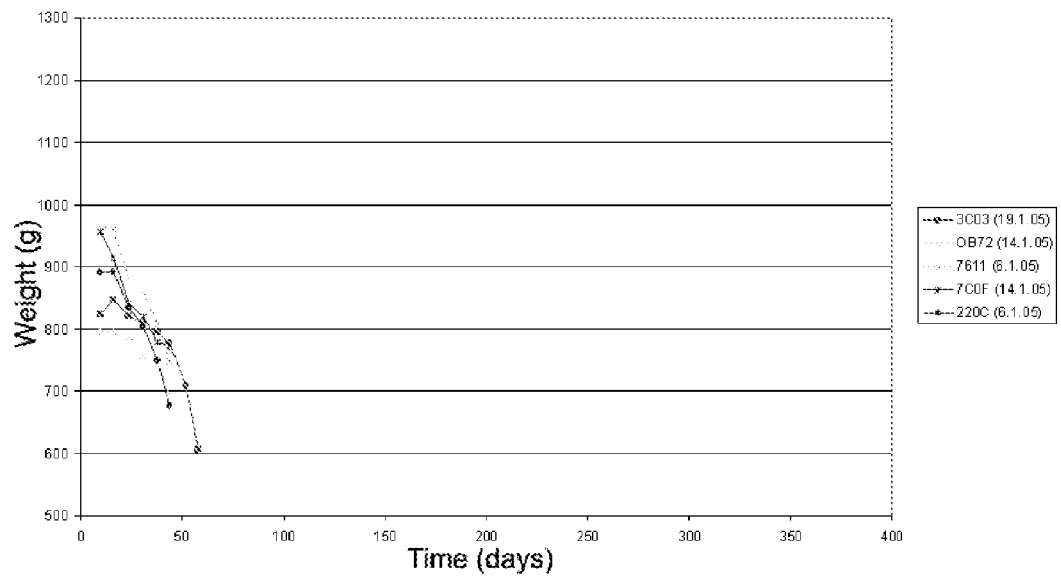
Fig. 14a₂
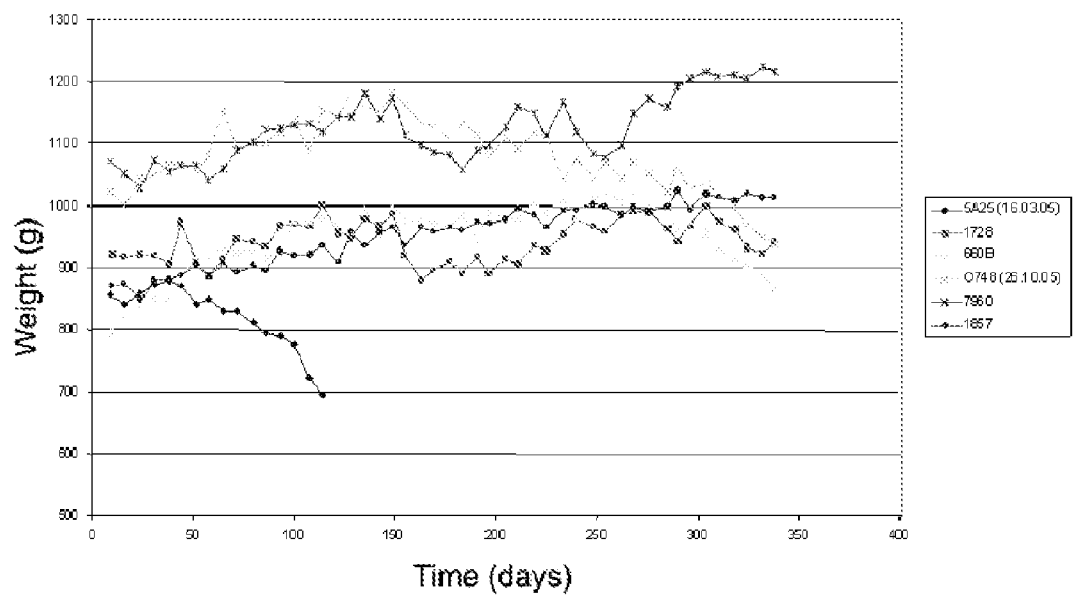
Fig. 14a₃

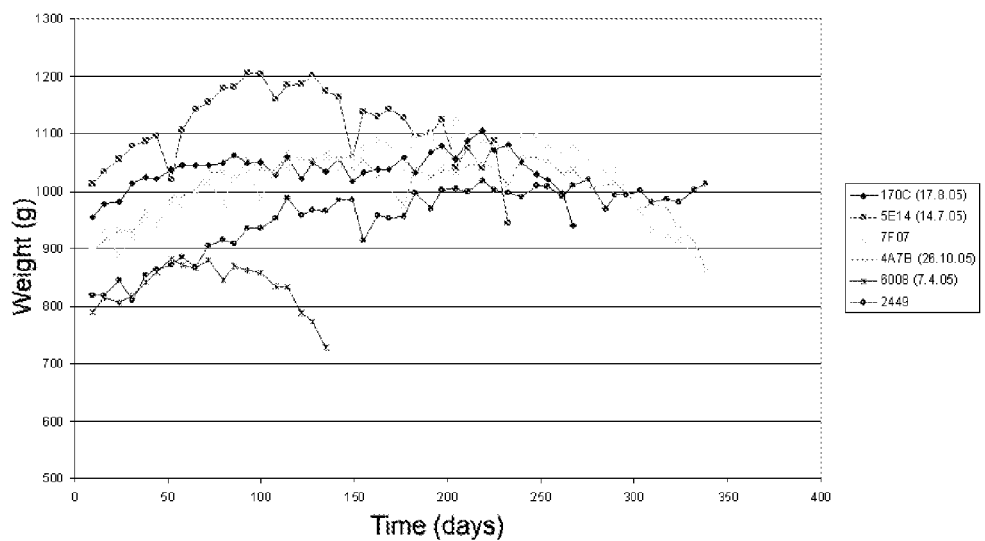
Fig. 14b₁
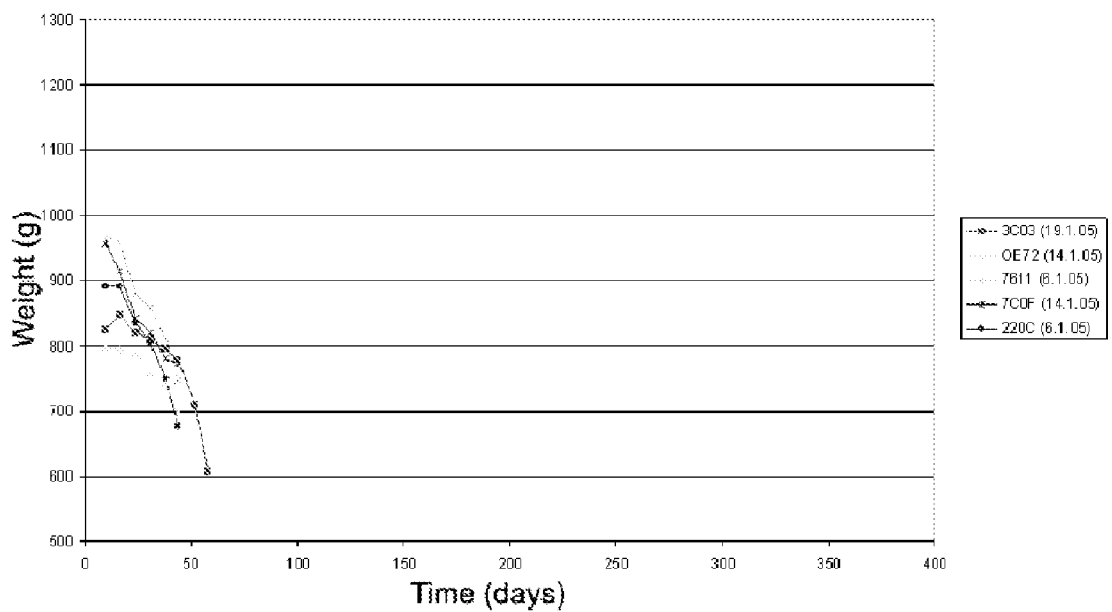
Fig. 14b₂

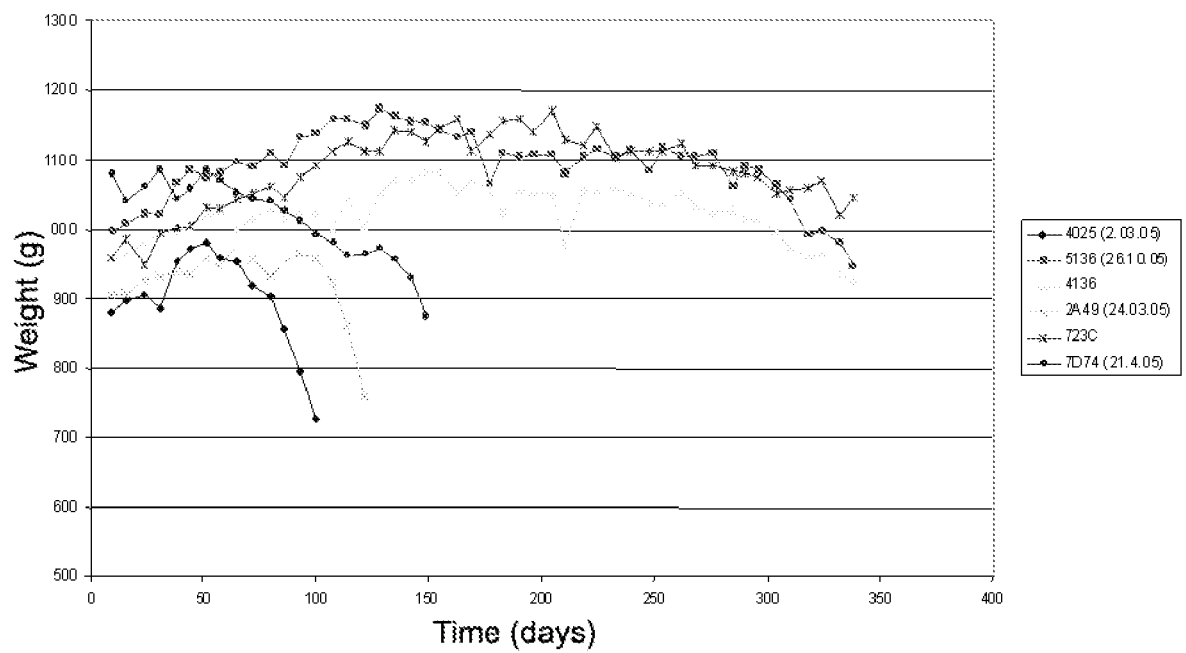
Fig. 14b$_3$

```
                        SEQUENCE LISTING

<160> NUMBER OF SEQ ID NOS: 4

<210> SEQ ID NO 1
<211> LENGTH: 24
<212> TYPE: DNA
<213> ORGANISM: artificial sequence
<220> FEATURE:
<223> OTHER INFORMATION: fadD26Fw synthetic primer of FadD26 gene

<400> SEQUENCE: 1
ctcgagttct ctatcctggt attc                                          24

<210> SEQ ID NO 2
<211> LENGTH: 20
<212> TYPE: DNA
<213> ORGANISM: artificial sequence
<220> FEATURE:
<223> OTHER INFORMATION: fadD26RV reverse primer fadD26 gene

<400> SEQUENCE: 2
ctcgaggttg gtcttgacag                                               20

<210> SEQ ID NO 3
<211> LENGTH: 28
<212> TYPE: DNA
<213> ORGANISM: artificial sequence
<220> FEATURE:
<223> OTHER INFORMATION: phoPF forward primer of phoP gene

<400> SEQUENCE: 3
aatctagatc aagcatcagc cgaggtac                                      28

<210> SEQ ID NO 4
<211> LENGTH: 28
<212> TYPE: DNA
<213> ORGANISM: artificial sequence
<220> FEATURE:
<223> OTHER INFORMATION: phoPR reverse primer of phoP gene

<400> SEQUENCE: 4
aatctagaga tcacccgaac gtagaacc                                      28
```

TUBERCULOSIS VACCINE

RELATED APPLICATIONS

The present application is a U.S. National Phase Entry of International Application No. PCT/ES2007/070051, filed Mar. 14, 2007, which claims priority to Spanish Patent Application no. P 200600761, filed Mar. 24, 2006, the entire disclosures of which are incorporated by reference herein.

BACKGROUND AND SUMMARY OF THE INVENTION

The present invention relates to an isolated microorganism belonging to the *Mycobacterium* genus, characterised in that it comprises the inactivation of the Rv0757 gene that confers a PhoP– phenotype and the inactivation of a second gene that prevents DIM production (DIM– phenotype). Additionally, the present invention comprises the use of said microorganism for the preparation of a vaccine for the immunization or prevention of tuberculosis.

The use of vaccines to prevent tuberculosis in humans has proved to be a tremendous challenge for almost a century now. BCG, derived from *M. bovis*, is currently the only tuberculosis vaccine in use and is the most widely used vaccine in the world. The development and generalised administration of the BCG vaccine since the beginning of the 1920s represented a significant advance, with the prospect of being able to eradicate tuberculosis from the world. However, these initial promises were not achieved and, from the results of a large number of efficacy trials, it is clear that the BCG vaccine in its current form is of limited use in controlling the disease, particularly in respiratory forms in adults in third world areas where the disease is endemic. Fine, P.E. Variation in protection by BCG: implications of and for heterologous immunity. *Lancet* 1995, 346(8986), 1339-1345. With more knowledge of the virulence of *M. tuberculosis* and immune response models that lead to the generation of protective immunity, it is possible to develop better vaccines than BCG. The observation that higher protection levels are achieved when the host is vaccinated with BCG suggests that viability and persistence are fundamental properties required for the success of a tuberculosis vaccine. In the present invention, we use a *M. tuberculosis* strain with the inactivated Rv0757 (phoP) gene and a second independent mutation of phoP, which prevents DIM synthesis, as a prototype single dose live vaccine, and we show that, as well as being more attenuated than BCG in immunocompromised SCID mice, it provided protection levels comparable to those conferred by BCG in mice and higher protection than BCG in guinea pigs.

The phoP gene, together with phoR, forms part of a two-component system that shows a high degree of similarity to other two-component systems that control the transcription of key virulence genes in intracellular pathogens. It also controls the expression of many other genes that are not directly involved in virulence. Groisman, E. A. The pleiotropic two-component regulatory system PhoP–PhoQ. *J Bacteriol* 2001, 183(6), 1835-1842. The elimination of virulence genes does not seem to be, per se, the only method for the attenuation of *M. tuberculosis*. It was shown that a pantothenate auxotrophic mutant of *M. tuberculosis*, which is incapable of de novo synthesis of pantothenic acid, persisted in SCID mice, without managing to cause the disease. Sambandamurthy, V. K., Wang, X., Chen, B. et al. A pantothenate auxotroph of *Mycobacterium tuberculosis* is highly attenuated and protects mice against tuberculosis. *Nat Med* 2002, 8(10), 1171-1174. Individual leucine auxotrophs are also strongly attenuated and incapable of replication in vivo in SCID mice. Hondalus, M. K., Bardarov, S., Russell, R., Chan, J., Jacobs, W. R., Jr. & Bloom, B. R. Attenuation of and protection induced by a leucine auxotroph of *Mycobacterium tuberculosis*. *Infect Immun* 2000, 68(5), 2888-2898. Therefore, the principle that vaccine strains based on *M. tuberculosis* can be successfully attenuated whilst retaining genes that are suppressed in *M. bovis* BCG is now generally accepted.

In the past, research into more effective vaccines than BCG was based on the notion that loss of virulence with BCG was in itself a factor that contributed to its lack of complete protective efficacy. Behr, M. A., Wilson, M. A., Gill, W. P. et al. Comparative genomics of BCG vaccines by whole-genome DNA microarray. *Science* 1999, 284(5419), 1520-1523. It was therefore reasoned that new attenuated mutants of *M. tuberculosis*, with less virulence, could be more effective as vaccines. However, a recent study has shown that natural infection with *M. tuberculosis* and vaccination with BCG do not differ in their capacity to bring about protective immunity against tuberculosis. Sampson, S. L., Dascher, C. C., Sambandamurthy, V. K. et al. Protection elicited by a double leucine and pantothenate auxotroph of *Mycobacterium tuberculosis* in guinea pigs. Infect Immun 2004, 72(5), 3031-3037. This raises questions as to whether or not it is possible to improve BCG by rational attenuation of *M. tuberculosis*. Within this context, the observation that the mutant *M. tuberculosis* strain of the present invention with the combination of 2 independent mutations 1.—in synthesis of the PhoP protein and 2.—in DIM synthesis is more attenuated than BCG in the SCID mouse model, even when applied at a dose 10 times higher than those of BCG, and the greater degree of protection than BCG in the guinea pig model is particularly surprising and significant.

BRIEF DESCRIPTION OF THE INVENTION

A first aspect of the invention relates to an isolated microorganism belonging to the *Mycobacterium* genus, characterised in that it comprises the inactivation of the Rv 0757 (phoP) gene and the inactivation of a second gene that prevents DIM (phthiocerol dimycocerosates) production. Hereinafter this isolated microorganism will be referred to as microorganism of the present invention.

A second aspect of the present invention relates to an isolated microorganism belonging to the *Mycobacterium* genus, characterised in that it comprises inactivating the Rv 0757 (phoP) gene and a second independent mutation of phoP that prevents DIM production. In a preferred aspect of the present invention, said second mutation is in the Rv2930 (fadD26) gene, consisting of the deletion of the fadD26 gene, which is essential for DIM synthesis.

A third aspect of the present invention relates to the use of the isolated microorganism of the present invention to prepare a vaccine for the prevention of tuberculosis in animals and still more preferably for the prevention of tuberculosis in humans, as well as other uses that tuberculosis vaccines currently have in the treatment of diseases in humans such as bladder cancer.

Hereinafter in the context of the present invention the "*M. tuberculosis* SO2 strain" will be used to refer to the isolated microorganism of the *M. tuberculosis* strain that has been inactivated by the Rv0757 gene constructed from the *M. tuberculosis* MT103 clinical strain by insertion of a kanamycin resistance marker at the BclI site of the Rv0757 gene of *M. tuberculosis* using homologous recombination according to the method described by Pelicic et al (1997) (Efficient allelic exchange and transposon mutagenesis in *Mycobacterium* tuberculosis. *Proc Natl Acad Sci USA* 94: 10955-10960) and which additionally comprises the inactivation of a second gene that prevents DIM (phthiocerol dimycocerosates) production. Therefore, said strain of the invention presents two independent mutations in live attenuated vaccines derived from *M. tuberculosis*, the independent phoP mutation not affecting the properties of the vaccine derived from the inactivation of said gene. Example 9 describes how to construct an isolated microorganism of the *Mycobacterium* genus with the independent double mutation that provides the same phenotype as described for the *M. tuberculosis* SO2 strain.

Hereinafter in the context of the present invention vaccine will be used to refer to those drugs whose administration produces defences against the disease to be prevented.

Hereinafter in the context of the present invention BCG will be used to refer to the current vaccine that has been in use against tuberculosis since 1921. It is a live attenuated vaccine derived from a *M. bovis* strain that lost its virulence after being subcultured in the laboratory and which we now know has more than one hundred deleted genes. Behr, M. A. BCG—different strains, different vaccines? *Lancet Infect Dis* 2002, 2(2), 86-92.

Hereinafter in the context of the present invention H37Rv will be used to refer to a pathogenic *M. tuberculosis* strain that has been sequenced, Cole et al. referring to these genes as Rv (Ref Cole et al 1998 Deciphering the biology of *Mycobacterium tuberculosis* from the complete genome sequence. *Nature* 393: 537-544).

Hereinafter in the context of the present invention MT103 will be used to refer to a *M. tuberculosis* clinical isolate. Camacho et al. 1999 Identification of a virulence gene cluster of *Mycobacterium tuberculosis* by signature-tagged transposon mutagenesis. *Mol Microbiol* 34: 257-267.

Hereinafter in the context of the present invention DIM− strain will be used to refer to the strain of the *M. tuberculosis* complex that is not capable of synthesizing phthiocerol dimycocerosates, which are important lipids related to the pathogenicity of *M. tuberculosis*. The 1A29 strain is used in FIG. 11, which consists of the MT103 strain with the Rv2930 (fadD26) gene inactivated by the transposon 1096 described in Camacho et al.

Hereinafter in the context of the present invention SO2+pSO5 will be used to refer to the *M. tuberculosis* SO2 strain in which the mutation in Rv0757 is complemented by the Rv0757 gene by transformation of a replicative plasmid with the mycobacterial phoP gene, but it is not capable of complementing DIM synthesis, its phenotype being phoP+ DIM−.

Hereinafter in the context of the present invention *M. tuberculosis* phoP− will be used to refer to the *M. tuberculosis* strain that has been inactivated by the Rv0757 gene by deletion between the EcoRV-BspEI sites, its phenotype being phoP− DIM+.

Hereinafter in the context of the present invention Rv2930 (fadD26) will be used to refer to the gene that is at the beginning of the operon that is responsible for the synthesis of phthiocerol dimycocerosates (Camacho et al.) and the elimination of this gene in *M. tuberculosis* confers a stable DIM− phenotype.

Other objects, advantages and novel features of the present invention will become apparent from the following detailed description of the invention when considered in conjunction with the accompanying drawings.

BRIEF DESCRIPTION OF THE DRAWINGS

FIG. 1 is a Western blot image of extracellular protein extracts.

FIGS. 2*a* and 2*b* shows attenuation of the SO2 strain of the present invention in SCID mice FIG. 3 shows cellular immune responses in mice vaccinated with the SO2 strain of the present invention and BCG.

FIGS. 4*a* and 4*b* shows the protective efficacy of SO2 of the present invention compared to BCG in vaccinated Balb/c mice.

FIGS. 5*a* and 5*b* shows the protective efficacy in guinea pigs vaccinated with the SO2 strain of the present invention and BCG against low doses of *M. tuberculosis* H37Rv.

FIGS. 6*a*-6*d* shows the protective efficacy in guinea pigs vaccinated with the SO2 strain of the present invention and BCG against infection with high doses of *M. tuberculosis* H37Rv.

FIG. 6*c* depicts low resolution (×30) images of representative sections of lung lobes taken from guinea pigs of each of the treatment groups. The bar represents 1 mm.

FIGS. 7*a* and 7*b* show the attenuation of intravenous infection with SO2 of the present invention in BalbC mice is not restored by complementing with phoP.

FIGS. 8*a* and 8*b* show that the SO2 strain does not produce DIM and DIM synthesis.

FIG. 9 shows the construction of plasmids for the inactivation of the fadD26 gene.

FIG. 10 shows the construction of plasmids for the inactivation of the phoP gene.

FIG. 11 shows the study of attenuation in mice.

FIG. 12 shows the weight curve of guinea pigs at 50 times the vaccine dose of SO2.

FIG. 13 shows the survival rate of vaccinated guinea pigs after infection with *M. tuberculosis*.

FIG. 14*$a_1$*-14*$b_3$* shows the weight curve of the studied guinea pigs after 400 days.

DETAILED DESCRIPTION

The Western blot analysis of FIG. 1 is a blot image of extracellular protein extracts of MT103, the SO2 strain of the present invention and BCG Pasteur, using polyclonal antibodies raised against PhoP and ESAT-6. The MT103 strain has a ESAT6+ and phoP+phenotype, the SO2 strain has a PhoP− and ESAT6+ phenotype and the BCG vaccine strain is PhoP+ and ESAT6

Attenuation of the SO2 strain of the present invention in SCID mice is illustrated by FIGS. 2*a* and 2*b*. The survival rate curve for aerosol infected SCID mice (n=10), with 20 CFUs of SO2, SO2 complemented with pSO5 (SO2+pSO5) and MT103. The mean number of days of survival was more than 245 days (SO2), 62.1±5.88 (SO2+pSO5) and 36.7±0.67 (MT103). The mice infected by aerosol with the SO2 strain survived for the 245 days of the experiment whereas those infected by MT103 and the SO2 strain complemented with phoP died before day 62 as shown in FIG. 2*a*. FIG. 2*b* depicts the survival rate curves for SCID mice (n=7) infected by intravenous injection with $5.4\times10^6$ CFUs of SO2 and $2\times10^5$ CFUs of BCG Pasteur. This shows that the attenuation level of the SO2 strain is greater than that of BCG, the tuberculosis vaccine currently used in humans.

The cellular immune responses in mice vaccinated with the SO2 strain of the present invention and BCG was also studied. Balb/c mice were vaccinated by subcutaneous injection with $8\times10^3$ CFU of BCG (Phipps) or $2.5\times10^3$ CFU of the SO2 strain of the present invention. The results are shown in FIG. 3 as a percentage of the total CD4+/CD8+ (populations in the spleen at intervals of time after vaccination and as a percentage of cells that express IFNγ of the total CD4+/CD8+ population after stimulation with complete *M. tuberculosis* antigen. * denotes statistically significant differences between the groups at the given points of time (p<0.005). The cellular immunity results show that the number of CD4+ lymphocytes in the animals vaccinated with the SO2 strain is greater on days 14, 30, 45 and 60 and the production of specific IFNγ against the *M. tuberculosis* antigens is significant on days 45 and 60 in relation to the mice vaccinated with BCG. The number of CD8+ lymphocytes in the animals vaccinated with the SO2 strain is greater on days 45 and 60 and the production of specific IFNγ against the *M. tuberculosis* antigens is significant on day 14 in relation to the mice vaccinated with BCG.

The protective efficacy of SO2 of the present invention compared to BCG in vaccinated Balb/c mice was measured by the number of CFUs recovered from lungs (FIG. 4*a*) and spleens (FIG. 4*b*) of Balb/c mice vaccinated with the SO2 strain of the present invention and BCG, intravenously infected with *M. tuberculosis* H37Rv. The reduction of CFUs in the lung and spleen of mice vaccinated with SO2 is similar to that obtained in those vaccinated with BCG and it shows significant protection in relation to the non-vaccinated mice.

The protective efficacy in guinea pigs vaccinated with the SO2 strain of the present invention and BCG against low doses of *M. tuberculosis* H37Rv was evaluated. Mean numbers of $\log_{10}$CFU/ml in the lungs (FIG. 5*a*) and spleens (FIG. 5*b*) of vaccinated guinea pigs and control guinea pigs injected with saline solution infected with low doses of *M. tuberculosis* H37Rv. The data represent the mean CFUs of all the animals (n=6) sacrificed after 4 weeks. Error bars indicate the standard deviation. The reduction in CFUs in the lungs and spleen of guinea pigs infected with *M. tuberculosis* at low doses and vaccinated with SO2 is similar to that obtained in those vaccinated with BCG and is significant in relation to the unvaccinated mice.

Given that the protection experiments in mice and in guinea pigs infected at low doses showed a clear protection in the mice vaccinated with SO2 and BCG but no differences between BCG and SO2, a guinea pig model with infection at high doses was used. Survival rate curve for guinea pigs after aerosol infection with *M. tuberculosis* H37Rv is illustrated in FIG. 6*a* while the extent of lung disease and spread of infection, measured by total lung consolidation, is shown in FIG. 6*b*. The values of each individual animal sacrificed at the human end point are marked with an "x". The broken line indicates the mean value in percentage of the group (# in SO2 corresponds to two animals). FIG. 6*c* is a low resolution (×30) of images of representative sections of lung lobes taken from guinea pigs of each of the treatment groups. The bar represents 1 mm. In FIG. 6*d*, mean CFU counts in the spleen and lungs of vaccinated and unvaccinated guinea pigs are compared. This experiment shows that with the guinea pig model at high doses of infection with *M. tuberculosis*, the guinea pigs vaccinated with SO2 survived significantly longer than with BCG vaccination and they also produced fewer lung lesions and had a lower number of CFUs in the spleen and lungs in relation to the current BCG vaccine.

Intravenous infection in Balb/C mice with 105 CFUs of the SO2 (phoP−DIM−) strain compared to the wild-type MT103 strain and the strain complemented with phoP (SO2+pSO5) was studied. The attenuation of intravenous infection with SO2 of the present invention in BalbC mice is not restored by complementing with phoP. A reduction in colonies (CFUs) was observed in both spleen (FIG. 7*a* spleen) and lung (FIG. 7*b* lung), measured after 3 and 6 weeks. The levels of CFUs of the wild-type strain were not restored in the complemented strain. These experiments in immunocompetent mice suggest that the surprising attenuation could be due to a second additional mutation that is not restored by phoP complementation.

Analysis of lipids from different strains of *M. tuberculosis* by thin layer chromatography shows the SO2 strain of the present invention does not produce DIM and DIM synthesis is independent of the phoP mutation. DIM production can be observed in FIG. 8*a* with the MT103 strain, whereas DIM is not produced with the SO2 strain and complementation with the phoP (SO2 pSO5) gene. This shows that with SO2 the absence of DIM is independent of phoP. FIG. 8*b* shows the MT103 strain and the MT103 strain inactivating only the phoP (MT103 ΔphoP::hyg) gene and both are capable of synthesising DIM, which confirms that DIM production is independent of the phoP mutation.

Construction of plasmids for the inactivation of the fadD26 gene is shown in FIG. 9. Construction of plasmids for the inactivation of the phoP gene is shown in FIG. 10.

Survival rate curve for Balb/C mice intratracheally inoculated to study the attenuation of the different strains of *M. tuberculosis* is shown in FIG. 11. H37Rv and MT103 correspond to strains of *M. tuberculosis* without mutations and all the mice died before the 10th week. With the *M. tuberculosis* DIM− (1A29) strain, 50% of the mice had survived after 20 weeks. All the animals inoculated with SO2 (phoP− and DIM− mutant) survived for the 20 weeks of the experiment.

To show that SO2 is not toxic six guinea pigs were inoculated with 50 times the vaccine dose. Their survival rate and weight curve was studied. The survival rate was 100% after the 6-month duration of the experiment. FIG. 12 shows the observed weight gain in all the animals over the 6 months, showing the non-toxicity of the SO2 strain (Y=weight in grams and week of infection. X=time in weeks).

The survival rate of vaccinated guinea pigs after infection with *M. tuberculosis* was studied (FIG. 13). The protection study in guinea pigs tracked the survival rate of guinea pigs, after 300 days. The survival rate curve was measure for unvaccinated guinea pigs (saline) and those vaccinated with the current BCG vaccine, with a *M. tuberculosis* phoP− strain or with SO2 (phoP− and DIM− mutant). After subcutaneous vaccination, the animals were infected with a virulent strain of *M. tuberculosis* (H37Rv) at a high dose to study the survival rate. After 60 days the 6 guinea pigs that had not been vaccinated (saline) had died, whilst the groups vaccinated with SO2, phoP− and BCG had survived. After 300 days of infection 3 guinea pigs vaccinated with BCG and phoP− had died, compared to only one of the group vaccinated with SO2, which indicates that the protection of the phoP mutant is similar to that of the current vaccine BCG, whereas vaccination with SO2, the phoP− and DIM− double mutant, protects better in the guinea pig model.

FIG. 14*a*$_1$-14*a*$_3$ show the survival after 400 days of the guinea pigs tracked in FIG. 13. The 6 unvaccinated guinea pigs had died after 60 days. After 400 days of infection 3 guinea pigs from the group vaccinated with SO2 (FIG. 14*a*) survived, whereas just 1 guinea pig vaccinated with BCG (FIG. 14*a* and FIG. 14*b*) and phoP− (FIG. 14*b*) had survived, indicating again that the protection of the phoP mutant is similar to that of BCG, whilst vaccination with SO2, the phoP− and DIM double mutant, protects better after the 400 days of the experiment.

One aspect of the present invention relates to an isolated microorganism belonging to the *Mycobacterium* genus, characterised in that it comprises the inactivation of the Rv0757 gene that confers a PhoP− phenotype and the inactivation of a second gene that prevents the DIM production (DIM− phenotype). Additionally, the present invention comprises the use of said microorganism for the preparation of a vaccine for the prevention of tuberculosis, and the vaccine per se.

Throughout the present invention, it is shown how isolated phoP– DIM– strains of the genus *Mycobacterium* present characteristics that make them particularly suitable for use as vaccines, due to both the level of attenuation, that they acquire and the level of protection that they confer.

In order to demonstrate the attenuation immunodepressed SCID mice were inoculated by aerosol with the SO2 (phoP–_ DIM–) strain. Said mice survive (FIG. 2a) significantly longer than mice infected by the wild-type strain. Additionally, this attenuation is complemented with phoP in the SO2+ pSO5 (phoP+DIM–) strain (FIG. 8a).

Figure 11:
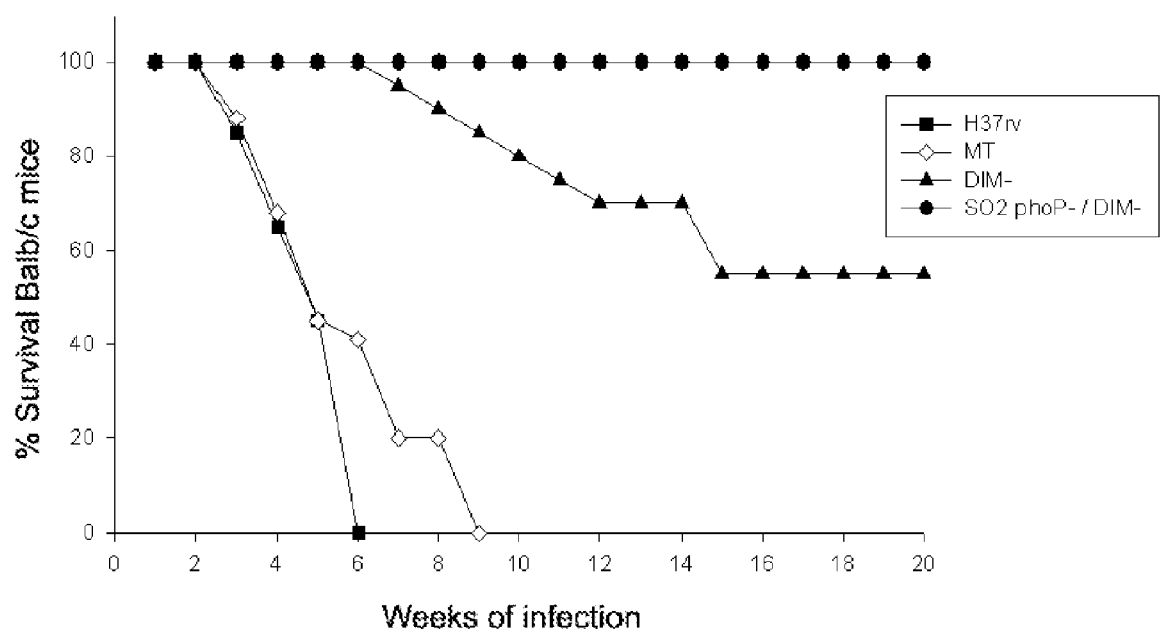

Moreover, when attenuation studies are carried out in immunocompetent Balb/C mice by intravenous injection (FIG. 7), there is a clear attenuation of SO2 in relation to the wild-type MT103 strain, but surprisingly this attenuation is not complemented with phoP, as the SO2+PSO5 (phoP+DIM–) strain is as virulent for the immunocompetent mouse as the wild-type strain. Survival studies in Balb/C mice comparing the SO2 (phoP– and DIM–) strain with just a DIM– strain show a surprisingly higher survival rate for SO2 (FIG. 11).

Figure 2A:
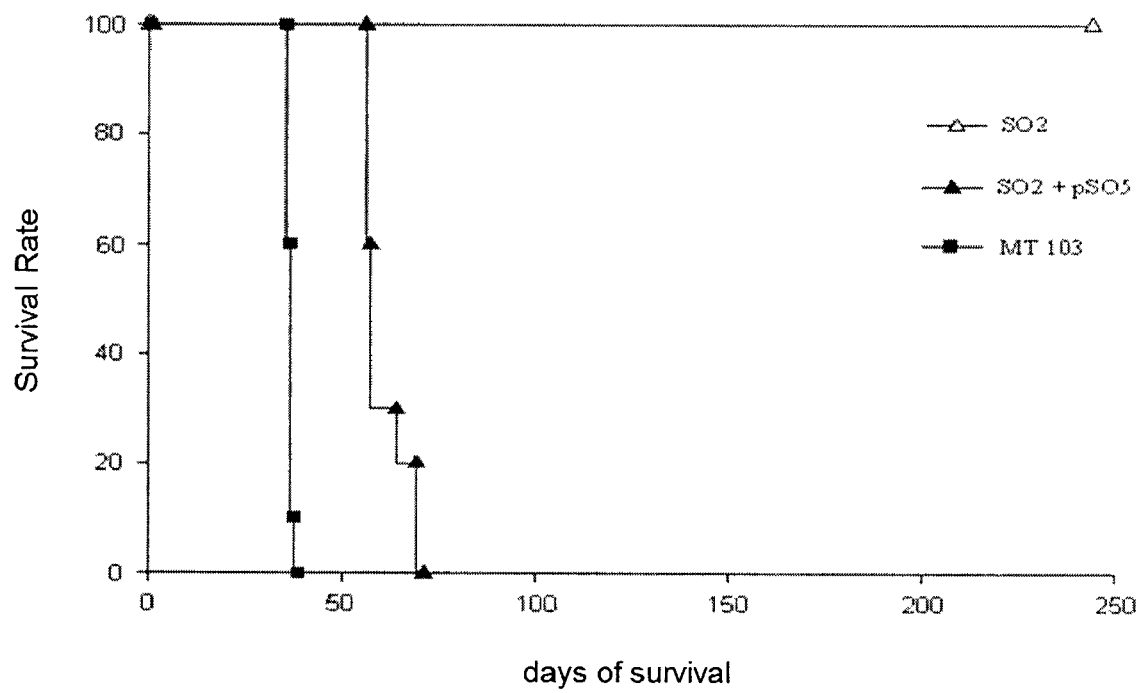
Figure 2B:
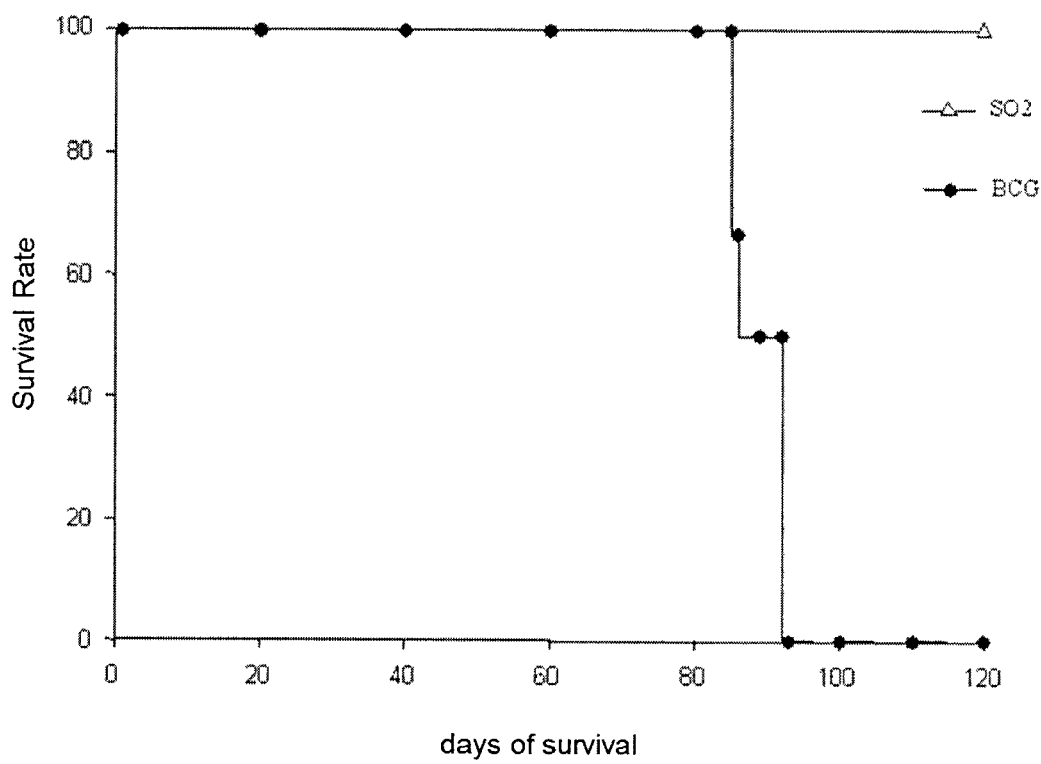
Figure 12:
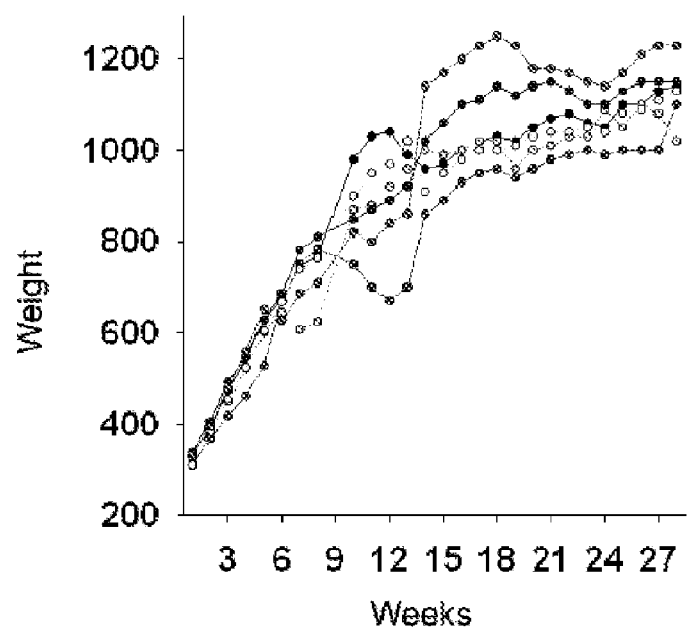

Comparative survival studies of SO2 and BCG in intravenously infected SCID mice show that the level of attenuation of the SO2 strain is higher than that of BCG, the vaccine that is currently used in humans against tuberculosis (FIG. 2b). Toxicity studies in guinea pigs with 50 times the dose of vaccine used in quality control for batches of BCG vaccine show that over the 6 months of the study the guinea pigs gain weight and do not present macroscopically or microscopically visible histological lesions that are compatible with tuberculosis, thereby confirming the attenuation and non-toxicity of SO2 (FIG. 12). This surprising attenuation and lack of toxicity is due to the PhoP– DIM– phenotype and also these mutations remain sensitive to antituberculosis drugs, which would allow a conventional treatment.

It is shown herein that in vaccination experiments carried out in Balb/c mice, the levels of protection conferred by the *M. tuberculosis* SO2 strain of the present invention and BCG were similar in both the lungs and the spleen up to four weeks after infection. If we compare the relative proportions of CD4+ and CD8+ cells from the spleens of vaccinated mice, in the mice vaccinated with the SO2 strain of the present invention a higher percentage of both CD4+ and CD8+ cells was found compared to the mice vaccinated with BCG. Furthermore, when these cells were stimulated with antigens derived from culture filtrate, a significantly higher percentage of CD4+/IFN-γ+ was measured in the mice vaccinated with the SO2 strain of the present invention 45 and 60 days after vaccination. Although it is not significant at each point of time, a similar tendency was measured for CD8+/IFN-γ+ in the mice vaccinated with the SO2 strain of the present invention. The data suggest that vaccination with the SO2 strain of the present invention results in better T cell activation compared to vaccination with BCG, measured by IFNγ synthesis. Given that protective immunity against *M. tuberculosis* generally depends on the generation of a $TH_1$-type cellular immune response characterised by the secretion of IFN-γ from the specific T cells of the antigen, it can be concluded that the relatively high levels of T cell activation induced by the SO2 strain of the present invention contributes to its capacity to confer a strong protective response.

Additionally, by using different systems and test models and a variety of conditions, we have managed to show the mouse model's relative capacity for studying the differences in protection of BCG compared to SO2. It was shown that the two vaccines, SO2 (phoP– DIM–) and BCG, confer protection in the mouse model.

A strategy was undertaken to compare the vaccines in a more significant and gradually more demanding trial with guinea pigs. This systematic approach to the comparison of vaccines could represent a useful starting point for identifying the best candidate vaccines for which further trials should be conducted. It is generally accepted that guinea pigs are more susceptible to infection by tuberculosis and could therefore be a more significant model for this disease. Baldwin, S. L., D'Souza, C., Roberts, A. D. et al. Evaluation of new vaccines in the mouse and guinea pig model of tuberculosis. *Infect Immun* 1998, 66(6), 2951-2959. The advantage of the guinea pig compared to mice is that the pathology of the disease is similar to that observed in tuberculosis in humans and it is therefore an appropriate model for testing the efficacy of a vaccine. In a recent aerosol vaccine study with a double pantothenate and leucine auxotrophic mutant of *M. tuberculosis*, protection levels equivalent to *M. bovis* BCG were obtained in the lungs and spleen of vaccinated guinea pigs, with limited spreading of the infection to the spleen induced by both vaccines, five weeks after aerosol application of *M. tuberculosis*. Sampson, S. L., Dascher, C. C., Sambandamurthy, V. K. et al. Protection elicited by a double leucine and pantothenate auxotroph of *Mycobacterium tuberculosis* in guinea pigs. *Infect Immun* 2004, 72(5), 3031-3037. In another study that used recombinant BCG that expressed ESAT-6, higher protection levels than *M. bovis* BCG were only observed in the spleen Pym, A. S., Brodin, P., Majlessi, L. et al. Recombinant BCG exporting ESAT-6 confers enhanced protection against tuberculosis. *Nat Med* 2003, 9(5), 533-539., suggesting that the improved protection is limited to its ability to prevent the infection from spreading from the lung.

To perform the present infection, guinea pigs were inoculated with a low dose of *M. tuberculosis* H37Rv, and the protection levels conferred by vaccination with the SO2 strain of the present invention and BCG were similar in both the lungs and the spleen up to 4 weeks after infection. Both vaccines provided extremely efficient protection, reducing the CFUs in the lungs and spleen by approximately 2 log. compared to the control groups, which received saline solution. However, there was no statistically significant difference between the two vaccine groups. In such a short period after infection, we can assume that it would be difficult to prove the greater efficacy of a new vaccine in relation to BCG. This is due to the fact that, at present, the CFUs (colony-forming units) of the organs of animals vaccinated with BCG are so low that the test does not have the differentiating capacity to show a significant additional reduction in CFUs. In other survival studies with guinea pigs it has been shown that, although vaccination with BCG provides a statistically significant protection compared to unvaccinated controls (or vaccinated with ineffective vaccines), this protection is only partial even against challenge with low doses of *M. tuberculosis*. In studies with an application of low doses conducted over 60 to 80 weeks after infection, some controls with BCG did not protect any of the guinea pigs, Horwitz, M. A. & Harth, G. A new vaccine against tuberculosis affords greater survival after challenge than the current vaccine in the guinea pig model of pulmonary tuberculosis, *Infect Immun* 2003, 71(4), 1672-1679, whilst others protected a low percentage (between 20 and 30%) of the animals, Brandt, L., Skeiky, Y. A., Alderson, M. R. et al. The protective effect of the *Mycobacterium bovis* BCG vaccine is increased by coadministration with the *Mycobacterium tuberculosis* 72-kilodalton fusion polyprotein Mtb72F in *M. tuberculosis*-infected guinea pigs. *Infect Immun* 2004, 72(11), 6622-6632 and Wiegeshaus, E. H., McMurray, D. N., Grover, A. A., Harding, G. E. & Smith, D. W. Host-parasite relationships in experimental airborne tuberculosis. 3. Relevance of microbial enumeration to acquired resistance in guinea pigs. *Am Rev Respir Dis* 1970, 102(3), 422-429. Application at a high dose, on the other hand, may result in more severe disease than that normally used to evaluate the protective efficacy of TB vaccines.

For the present invention we used aerosol infection with a relatively high dose of *M. tuberculosis* H37Rv and the study period was extended to 180 days. We did this to generate a more demanding level of challenge that could show the potential protective efficacy of the SO2 strain of the present invention, and at the same time to facilitate a level of discrimination in relation to BCG. In terms of survival, the animals of the group vaccinated with BCG were significantly protected in comparison with the unvaccinated controls, and they showed an overall protection level similar to that observed in other studies, despite the relatively high dose of infection used in our study. Moreover, we also found a statistically significant increase in the protective efficacy of the SO2 (phoP– DIM–) strain of the present invention in comparison with BCG, measured by several indicators, including prolonged survival and the degree of consolidation of pulmonary lesions. This less severe form of disease could have been directly responsible for the higher survival rate of the animals vaccinated with the SO2 strain of the present invention.

The results described in the present invention show that the SO2 strain and therefore a microorganism belonging to the *Mycobacterium* genus (particularly from the *M. tuberculosis* complex) with phoP– DIM– phenotype is a more effective vaccine than BCG in accordance with a number of criteria. It is more attenuated than BCG in SCID mice, it provides mice with a protective immunity that is as least as good as BCG and it generates stronger cellular immune responses. Additionally, in protection experiments conducted in guinea pigs against infection with high doses of H37Rv, the strain with phenotype DIM– phoP– results in a 100% survival rate of guinea pigs in circumstances in which BCG only achieve a 33% survival rate. This protection is linked to a reduction in the severity of the disease and the bacterial load.

In order to check whether the protection level of SO2 (phoP– DIM–) was due to the phoP mutation or whether it might be due to the additional mutation in DIM, another vaccination experiment was carried out in guinea pigs with high doses of infection. Groups of 6 animals were vaccinated with BCG, with SO2 (PhoP– DIM–) and with *M. tuberculosis* phoP– DIM+ and 6 animals used as a control were not vaccinated. The experiment lasted 400 days.

In this other experiment the unvaccinated guinea pigs died before day 70. After 300 days of infection 3 guineas pigs vaccinated with BCG and phoP– DIM+ had died, compared to only one in the group vaccinated with SO2, which suggests that the protection provided by the phoP– DIM+ mutant is similar to the current vaccine BCG, whilst vaccination with SO2, the double phoP– and DIM– mutant, protects better in the guinea pig model (FIG. 13). After 400 days 3 guinea pigs in the group vaccinated with SO2 (FIG. 14*a*) had survived, whereas only 1 guinea pig vaccinated with BCG (FIG. 14*a* and FIG. 14*b*) and phoP– DIM+ (FIG. 14*b*) had survived, indicating that the protection of the phoP– DIM+ mutant is similar to BCG, whilst vaccination with SO2, the phoP– and DIM– double mutant, protects better after the 400 days of the experiment, the surprising effect of greater protection than BCG being attributed not only to the phoP– mutation but to the SO2 double mutation phoP– DIM–.

Therefore, a first aspect of the present invention relates to an isolated microorganism belonging to the *Mycobacterium* genus, characterised in that it comprises the inactivation or deletion of:

a. the phoP gene or one or more genes that regulate the phoP gene or that are regulated by phoP and b. a second gene that prevents DIM production.

In a preferred embodiment of the invention the isolated microorganism of the invention is characterised in that the phoP gene is inactivated through the inactivation or deletion of the Rv0757 gene.

In a more preferred embodiment of the invention the isolated microorganism of the invention is characterised in that DIM production is inactivated through the deletion or inactivation of the Rv2930 (fadD26) gene.

In an even more preferred embodiment of the invention, the isolated microorganism of the invention is characterised in that it comprises the deletion or inactivation of the Rv2930 and Rv0757 genes.

In another embodiment of the invention, the isolated microorganism of the invention is characterised in that the species of the *Mycobacterium* genus belongs to the *Mycobacterium tuberculosis* complex.

A second aspect of the invention relates to the process for preparing the isolated microorganism of the invention, which comprises:

a. The inactivation or deletion of the phoP gene or one or more genes that regulate the phoP gene, preferably the inactivation or deletion of the Rv0757 gene, and b. The inactivation or deletion of a second gene that prevents DIM production, preferably the deletion or inactivation of the Rv2930 (fadD26) gene.

A third aspect of the invention relates to a vaccine (hereinafter the vaccine of the invention) to immunize an individual against the symptoms caused by tuberculosis, wherein said vaccine comprises at least one isolated microorganism of the invention.

In a preferred embodiment of the invention, the vaccine also comprises pharmacologically acceptable excipients.

A fourth aspect of the invention relates to the process for preparing a medicine, preferably a vaccine, which comprises the incorporation of an isolated microorganism of the invention to a suitable medium for administration in humans or animals in a therapeutically effective dose and, optionally, the addition of excipients that are pharmacologically suitable for the production of vaccines.

Said medicine is suitable for the treatment of bladder cancer, for the treatment or prevention of tuberculosis, or as a vector or adjuvant, preferably to immunise an individual against the symptoms caused by tuberculosis.

A fifth aspect of the invention relates to the use of the isolated microorganism of the invention to prepare the vaccine of the invention for the prevention and/or treatment of tuberculosis in humans or animals.

Throughout the description and claims the word "comprise" and its variants do not imply the exclusion of other technical characteristics, additives, components or steps. For a person skilled in the art, other objects, advantages and characteristics of the invention will arise partly out of the description and partly when the invention is put into practice. The following examples and figures are provided by way of a non-limiting, illustrative example of the present invention.

EXAMPLES

Example 1

Materials and Methods 1.1.—Protein Extraction and Immunoblotting.

Polyclonal antibodies against the PhoP protein were obtained, which received four doses of PhoP (0.5 mg), in weeks 0, 4, 8, 12 and 16, respectively. The anti-PhoP antibodies were detected using the ELISA test (ZEU-Immunotec Zaragoza, Spain). Monoclonal antibodies against ESAT-6 were kindly supplied by Pym, A. S., Brodin, P., Brosch, R., Huerre, M. & Cole, S. T. Loss of RD1 contributed to the attenuation of the live tuberculosis vaccines *Mycobacterium bovis* BCG and *Mycobacterium microti*. *Mol Microbiol* 2002, 46(3), 709-717. Cell-free protein extracts of mycobacteria were prepared from early cultures in log-phase that were grown in Middlebrook 7H9-ADC broth, following the usual methods. Sambrook, J. a. R., D W. *Molecular Cloning a laboratory manual*, Cold Spring Harbor Laboratory Press, New York, 2001. The *M. tuberculosis* protein extracts were filtered through a Millex-GP filter with a pore size of 0.22 μm (Millipore, Bedford, Mass.). The *M. tuberculosis* H37Rv culture filtrate cultured for 5-6 weeks was collected and the culture filtrate proteins were precipitated with 45% (w/v) ammonium sulphate. The Western Blot analysis was carried out according to the normal methods. Goat anti-rabbit antibodies labelled with horseradish peroxidase (Bio-Rad Laboratories, Hercules, Calif.) were used as secondary antibodies.

1.2.—Infection of SCID Mice with *M. tuberculosis*.

The work with SCID mice was carried out under the supervision of the Animal Care Committee at the "Germans Trias i Pujol" University Hospital, in accordance with EU laws on the protection of laboratory animals. SCID CB-17/Icr Ico specific pathogen free (spf) mice were obtained from Charles River (Bagneux Cedex, France). For aerosol infection, mice were placed in the exposure chamber of an airborne infection apparatus (Glas-col Inc., Terre Haute, Ind., USA). The nebuliser compartment was filled with 7 ml of a *M. tuberculosis* suspension to provide an approximate uptake of 20 viable bacilli within the lungs. Ten mice were used for each experimental group. For intravenous infection, groups of 7 mice were infected with 200 μl of PBS containing doses equivalent to $2 \times 10^5$, $2 \times 10^4$ and $2 \times 10^3$ of viable BCG and $5.4 \times 10^6$, $5.4 \times 10^5$ and $5.4 \times 10^4$ of viable *M. tuberculosis* phoP strain by a lateral tail vein. The significance of differences in survival times between treated mice was determined using the Mantel-Haenszel test. Viable counts were performed on serial dilutions of the homogenate, plated onto Middlebrook 7H11+ OADC agar and examined after 3 weeks for growth. For histological analysis, the tissues were fixed in buffered formol-saline solution and embedded in paraffin. Five-μm thick sections were cut and stained with Ziehl-Neelsen stain.

1.3.—Determination of the Activation of Cellular Immunity in Balb/c Mice after Subcutaneous Vaccination with SO2 of the Present Invention and BCG.

Groups of four Balb/C mice were sacrificed on days 7, 14, 21, 28, 45 and 60 after subcutaneous vaccination with $8 \times 10^3$ CFU of BCG (Phipps) or $2.5 \times 10^3$ CFU of the SO2 strain of the present invention. The spleens were removed and placed in 2 ml of RPMI medium and 10% foetal calf serum (GIBCO. Invitrogen Corporation) containing 0.5 mg/ml type-II collagenase (Worthington, N.J., USA), and 2 U/ml DNase (GIBCO), and incubated for 1 hour at 37° C., with 5% CO2. They were then passed through a 70 μm cell sieve (Falcon, Becton Dickinson 70 μm Nylon 35-2350), crushed with a syringe plunger and rinsed with medium. The cells were centrifuged, the supernatant was discarded and the red cells were removed with lysis buffer. Arriaga, A. K., Orozco, E. H., Aguilar, L. D., Rook, G. A. & Hernandez Pando, R. Immunological and pathological comparative analysis between experimental latent tuberculous infection and progressive pulmonary tuberculosis. *Clin Exp Immunol* 2002, 128(2), 229-237. After centrifuging and washing with RPMI medium, the cells were resuspended in FACS buffer (PBS 1×, pH 7.2, 1% BSA), and were counted. The cell surface was labelled by incubating $10^6$ cells with 100 μl of anti-CD4-FITC or anti-CD8-FITC monoclonal antibodies, diluted at 1:20 in PBS containing 1% BSA and 0.1% sodium azide for 20 min at 4° C., and analysed using a FACScan cytometer.

The *M. tuberculosis* H37Rv strain was cultured in Middlebrook 7H9 medium (Difco Laboratories) supplemented with OADC (Difco Laboratories). After 1 month of culture, the bacterial mass was separated and the culture filtrate was collected. The antigens of said filtrate were precipitated with 45% (w/v) ammonium sulphate, washed and dissolved again in PBS. To stimulate the cells, $1 \times 10^6$ spleen cells were resuspended in 100 μl RPMI medium per well, and incubated with 10 μg *M. tuberculosis* culture filtrate antigens, suspended in 100 μl PBS for 72 hours at 37° C. with 5% CO2. The cells and the culture medium were centrifuged, the supernatant was discarded and, after counting and checking the viability, $2.5 \times 10^5$ cells per tube were labelled on the surface of CD4+ or CD8+ cells, as has been described above. After washing, the cells were resuspended and incubated for 20 min at 4° C. in 0.1% saponin dissolved in PBS. Intracellular IFN-γ was detected by incubating the cell for 20 min at 4° C. in the dark, with 100 μl of a 1/20 dilution of monoclonal anti-IFN-γ labelled with phycoerithrin (PE). The cells were fixed with 100 μl of 4% paraformaldehyde diluted in PBS. The samples were analysed after 20 minutes using a FACScan cytometer. The isotype controls were Ab-FITC (1:20 dilution)+Ab-PE (1:20 dilution).

1.4.—Protective Efficacy of SO2 of the Present Invention in Balb/c Mice.

All of the animals were kept in controlled conditions in the P3 High Security Laboratory of the Animal Facility at the Pasteur Institute in Paris, in accordance with EU directives on the protection of laboratory animals. Groups of Balb/c mice (7 per group) were subcutaneously vaccinated at the base of the tail with $10^7$ CFUs of the SO2 strain of the present invention or BCG (Pasteur). Eight weeks after vaccination, all the mice were intravenously injected with $2.5 \times 10^5$ CFU of *M. tuberculosis* H37Rv. Four weeks after injection, the mice were sacrificed. Viable counts were performed on serial dilutions of the homogenate, cultured in Middlebrook 7H11+ agar OADC broth, and after 3 weeks the growth of *M. tuberculosis* H37Rv of the SO2 strain of the present invention was examined on the basis of the kanamycin resistance phenotype of the latter strain.

1.5.—Protective Efficacy of SO2 of the Present Invention in Guinea Pigs.

The experimental work with guinea pigs was carried out in accordance with UK laws on experiments on animals and was approved by a local ethics committee of the Health Protection Agency, Porton Down, UK. Female Dunkin-Hartley guinea pigs were obtained from approved commercial suppliers (UK Home Office) (David Hall, Burton-on-Trent, UK or Harlan Ltd UK, Bicester, UK), and they were reared in complete isolation. The results presented in FIG. 6 show that the SO2 strain confers greater protection than BCG. The results presented in FIG. 13 and FIG. 14 show that this surprising protection of the SO2 mutant is due to its double phenotype DIM−/PhoP−.

1.6.—Low Dose Application.

Groups of 6 guinea pigs were subcutaneously vaccinated in the back of the neck with 250 µl of: $5\times10^4$ CFUs of BCG Pasteur; $5\times10^4$ CFUs of SO2 of the present invention; or with saline solution. The animals were rested for a period of 12 weeks before aerosol challenge using a contained Henderson apparatus, as has been described above. Williams, A., Davies, A., Marsh, P. D., Chambers, M. A. & Hewinson, R. G. Comparison of the protective efficacy of bacille calmette-Guerin vaccination against aerosol challenge with *Mycobacterium tuberculosis* and *Mycobacterium bovis*. *Clin Infect Dis* 2000, 30 Suppl 3, S299-301. Aerosols were generated from fine particles of *M. tuberculosis* H37Rv, with a mean diameter of 2 µm, (diameter range: 0.5-7 µm) using a Collison nebuliser, and applied directly to the animal's snout. The aerosol was generated from a suspension in water containing $2\times10^6$ CFU/ml to achieve a retained inhaled dose that was calculated to be approximately 10-50 CFU/lung.

Four weeks after application the protection was evaluated. The animals were sacrificed by a peritoneal overdose of sodium pentobarbital. Tissue was aseptically removed from the spleen and lungs (the left and middle cranial lobes, right middle lobe and right caudal lobes) and placed in sterile receptacles. The material was stored at −20° C. and was then prepared to count the number of bacteria. The tissue was homogenized in 10 ml (lung) or 5 ml (spleen) of sterile deionized water using a rotating blade macerator system (Ystral). Viable cell counts were performed on serial dilutions of the homogenate, cultured in Middlebrook 7H11+ agar OADC, and *M. tuberculosis* growth was examined after 3 weeks. The data were transformed into $\log_{10}$ for their analysis and the numbers of viable *M. tuberculosis* for each vaccine group were compared with the control group with saline solution by Student's t-test.

1.7.—Protection Test in Guinea Pigs after Infection with a High Dose of *M. tuberculosis*.

Groups of 6 guinea pigs were subcutaneously vaccinated with $5\times10^4$ CFU of SO2 of the present invention or BCG (Danish 1331) 10 weeks before aerosol application with *M. tuberculosis*. The aerosol application was performed as described in the previous paragraph, using a suspension of $5\times10^7$ CFU/ml to provide the lungs with around 500 CFU. After application, the animals were kept at containment level 3 (ACDP), changes in weight were regularly controlled and they were humanely sacrificed 180 days after application or at the human end point (loss of 20% of the maximum body weight). The post-mortem sample collection and processing were carried out as described above, except that lung consolidation was measured using image analysis of sections of lung tissue fixed in formalin, stained with Haematoxylin and Eosin (H+E). Animal survival was compared using Kaplan Meier survival estimates and Log Rank distribution analysis was used to identify the statistically significant differences. The CFU and lesion consolidation data were analysed by ANOVA, using Fisher's pairwise comparisons to compare the mean values of the groups.

Example 2

Characterisation of *M. tuberculosis* phoP

Evidence for the involvement of the phoP gene in global regulation of mycobacteria genetic circuits was provided by the observation of changes in bacillus size and cording properties of growing cells harbouring the inactivated phoP gene. Given the key properties of secreted antigens as determinants of protection against tuberculosis, we hoped to determine whether the pleiotropic effects of the phoP gene mutation extended to influence synthesis of the major immunodominant antigen: ESAT-6. Western blot analysis was carried out on the SO2 strain, BCG and MT103, using antibodies raised against the PhoP protein and ESAT-6. The results clearly showed that the PhoP protein was expressed constitutively in the *M. tuberculosis* MT103 and BCG strains, whilst it was completely absent in the SO2 strain of the present invention. In contrast, the levels of expression of ESAT-6 in the supernatant of cultures of the SO2 strain were similar to those detected from the parental strain of MT103 and, as expected, no ESAT-6 protein was detected in BCG.

Example 3

Survival of Mice Infected with the Strains of the Present Invention and BCG

The survival of immunocompromised SCID mice was evaluated after aerosol infection (approximately 20 CFU) with the MT103 strain, with SO2 and with SO2 complemented with the phoP gene (SO2+pSO5). Perez, E., Samper, S., Bordas, Y., Guilhot, C., Gicquel, B. & Martin, C. An essential role for phoP in *Mycobacterium tuberculosis* virulence. *Mol Microbiol* 2001, 41(1), 179-187. All of the mice infected with SO2 survived for more than 245 days. In contrast, all of the SCID mice infected with MT103 or complemented *M. tuberculosis* S02-pSO5 had died 62 days after infection, indicating a recovery of the virulence of the complemented strain (FIG. 2a).

The attenuation of the SO2 strain was also compared with BCG in SCID mice after intravenous administration. Groups of SCID mice were inoculated with a number of doses ($2\times10^5$, $2\times10^4$ and $2\times10^3$ CFU) of BCG Pasteur or the SO2 strain ($5.4\times10^6$, $5.4\times10^5$ and $5.4\times10^4$ CFU) by a lateral tail vein. Histological staining of the infected alveolar macrophages of a subgroup of mice sacrificed three weeks after infection revealed a smaller number of alcohol-acid resistant bacilli in the lungs of mice infected with the *M. tuberculosis* SO2 strain, compared with BCG. All the mice inoculated with the higher doses of BCG ($2\times10^5$ CFU) had died 92 days after infection (mean survival time: 89±3.5 days) (FIG. 2b). In contrast, all of the mice infected with the highest dose of SO2 ($5.4\times10^6$ CFU) had survived after 120 days (FIG. 2b). At the time of death, the bacterial loads of the lungs of mice infected with BCG, $2\times10^5$ CFU, were at least 100 times higher, if compared with the mice infected with SO2, $5.4\times10^6$ CFU.

Example 4

Quantitative CD4+ and CD8+ Responses of Vaccinated Balb/c Mice

Figure 3:
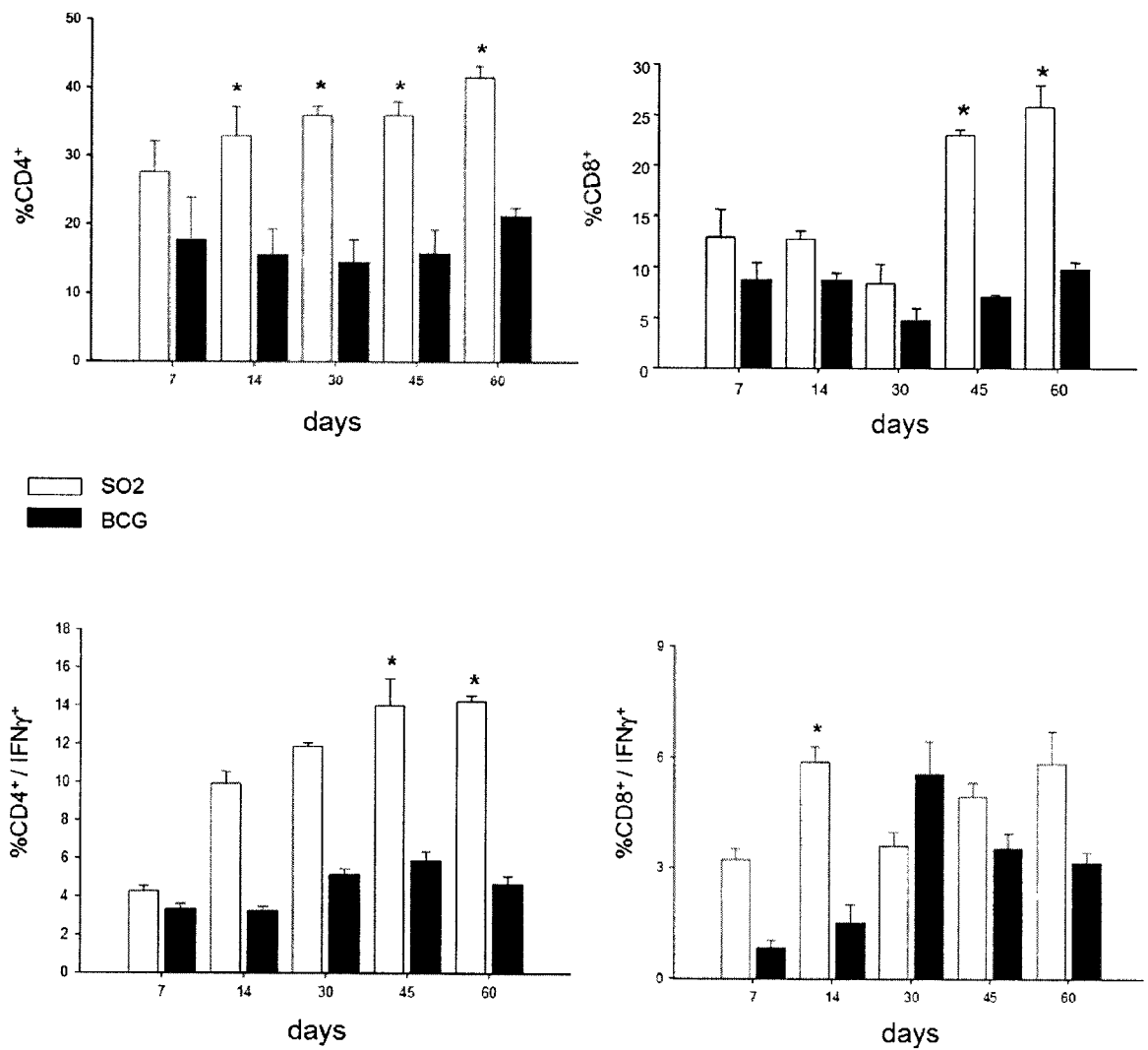

To compare the activation of cellular immunity induced by vaccination with SO2 of the present invention and BCG, on days 7, 14, 30, 45 and 60 after vaccination, cell suspensions were collected from the spleen of groups of at least four Balb/c mice subcutaneously vaccinated with the SO2 strain of the present invention and BCG Phipps, and the relative proportions of CD4+ and CD8+ cells were determined by cytofluorometry (FIG. 3). Vaccination with SO2 induced a significantly higher number of CD4+ cells 14 days after vaccination, compared to vaccination with BCG, and a significantly higher number of CD8+ cells after 45 days. These splenocytes were stimulated with total antigens derived from *M. tuberculosis* culture filtrate. After 3 days, the lymphocyte populations were analysed by flow cytometry, and specific antibodies were combined for the detection of CD4+/CD8+ cells and intracellular synthesis of IFN-γ. Vaccination with SO2 induced a significantly higher proportion of CD4+/IFN-γ+ producing cells 45 days after vaccination, compared with BCG (FIG. 3). After a certain point in time, the proportion of cells that produced CD8+/IFN-γ+ was always higher in the SO2 group (significantly different on day 14).

Example 5

Protective Immunity Generated by SO2 of the Present Invention in Balb/c Mice

Figure 4A:
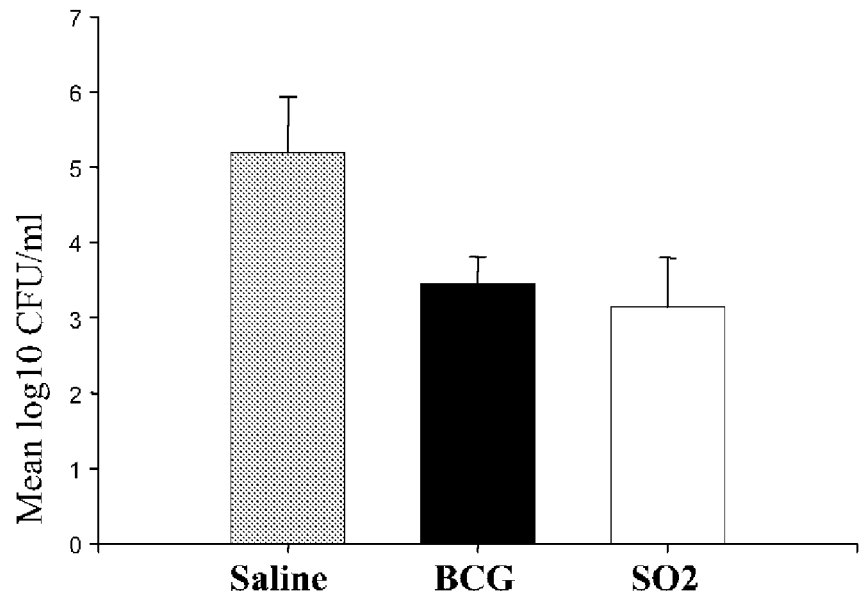
Figure 4B:
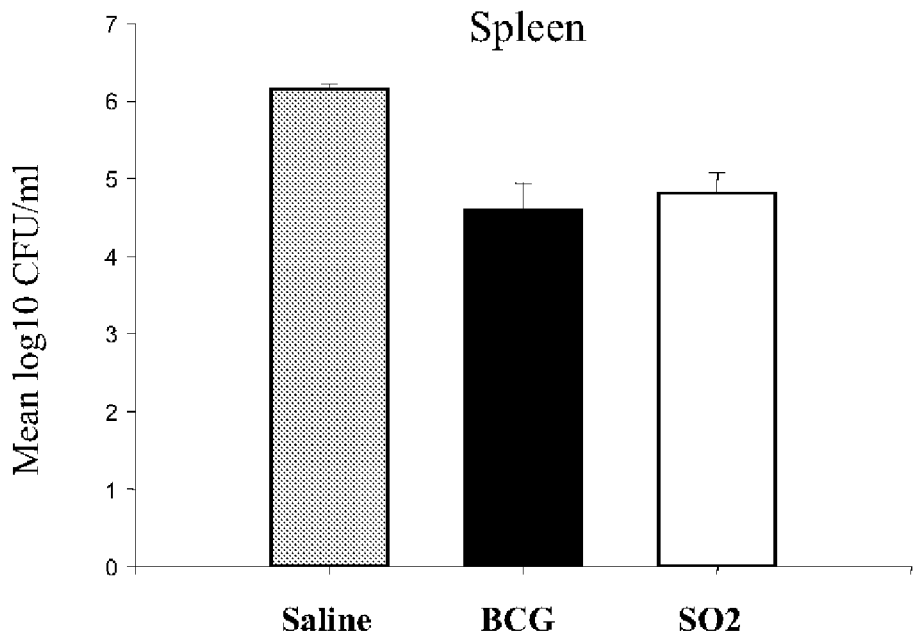

Having proven that the SO2 strain of the present invention was attenuated in SCID mice, we were interested to determine whether the observed reduction in virulence would confer some kind of protective property on the mutant strain. We subcutaneously vaccinated Balb/c mice with the SO2 strain of the present invention or with BCG (Pasteur). Eight weeks after vaccination, all of the mice were intravenously injected with $2.5 \times 10^5$ CFU of *M. tuberculosis* H37Rv. The mice were sacrificed 4 weeks after injection. The protection levels were determined by evaluating the numbers of viable *M. tuberculosis* H37Rv recovered from the lungs and spleen of both groups of mice (FIG. 4). Both vaccines conferred similar but significant levels of protection, if compared with the controls treated with saline solution ($p<0.05$). Inhibition of *M. tuberculosis* H37Rv growth was recorded in both the lungs and the spleen, with reductions of approximately 1.5 $\log_{10}$ and 1.3 $\log_{10}$CFU, respectively.

Example 6

Protective Immunity of SO2 of the Present Invention in Guinea Pigs

The results obtained in mouse vaccination experiments indicated that the attenuation of the SO2 strain of the present invention gave it vaccine properties similar to those of BCG Pasteur. However, it is generally accepted that guinea pigs are a more appropriate model for human tuberculosis, with many similarities in terms of the progression and pathology of the disease. This animal model is therefore a more appropriate system for evaluating the efficacy of a vaccine. To investigate the protective efficacy of the SO2 strain of the present invention, we carried out experiments that involved aerosol application to vaccinated animals at low doses (10-50 CFU) and at high doses (500 CFU). Groups of six guinea pigs were subcutaneously vaccinated with SO2 of the present invention or with BCG. Ten weeks after vaccination, all the guinea pigs were administered inhaled doses of *M. tuberculosis* H37Rv.

Figure 5A:
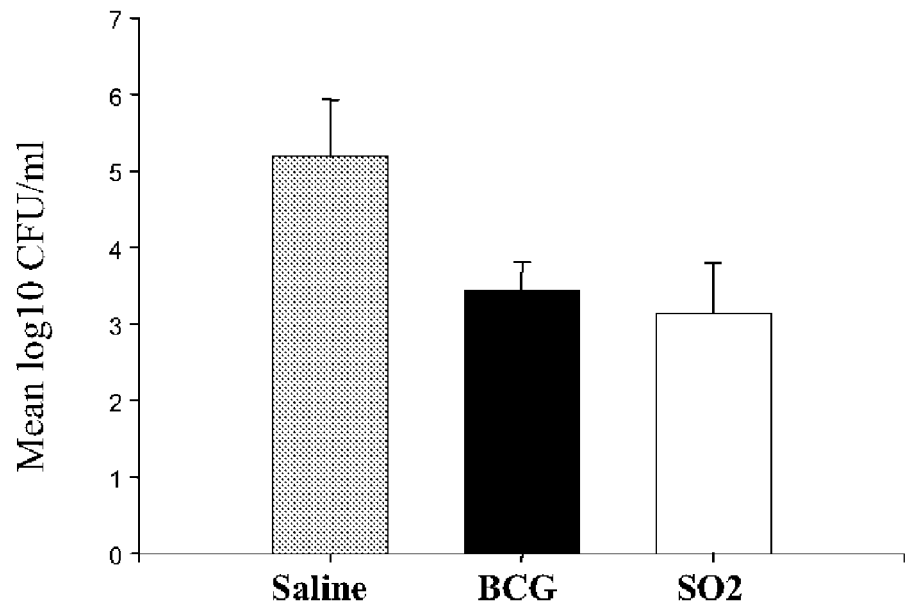
Figure 5B:
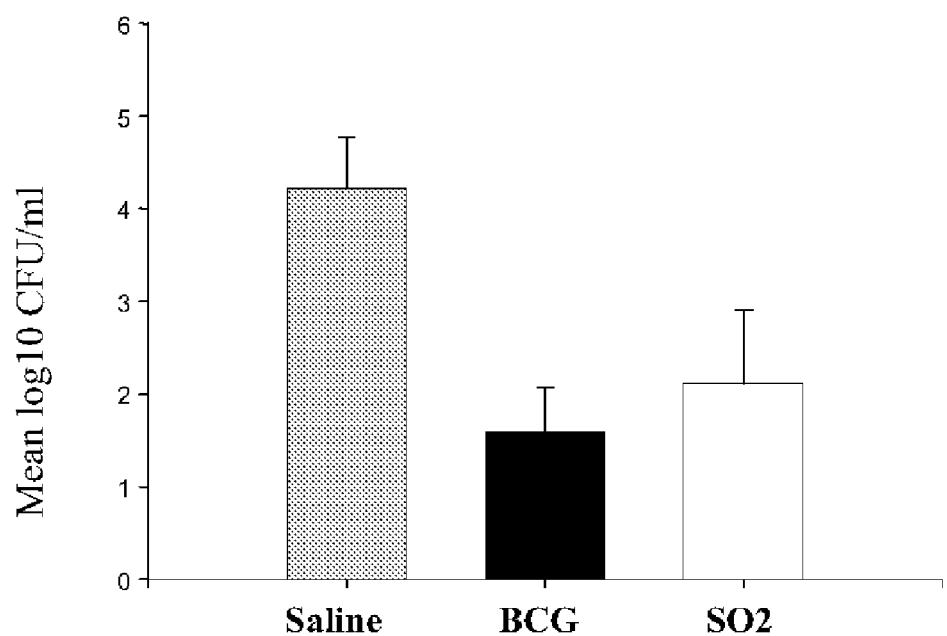

The animals that received the lower dose were sacrificed after 4 weeks, and the bacterial loads in the lungs and spleen were counted. The protective efficacy was determined by comparing the numbers of viable *M. tuberculosis* H37Rv recovered from the organs of guinea pigs in each treatment group. In this experiment, the reduction of CFUs in the lungs and spleen was significantly different between the unvaccinated control animals and those vaccinated with BCG or *M. tuberculosis* SO2 ($p=0.005$). However, no significant difference was found between the vaccinated groups (FIG. 5).

Figure 6A:
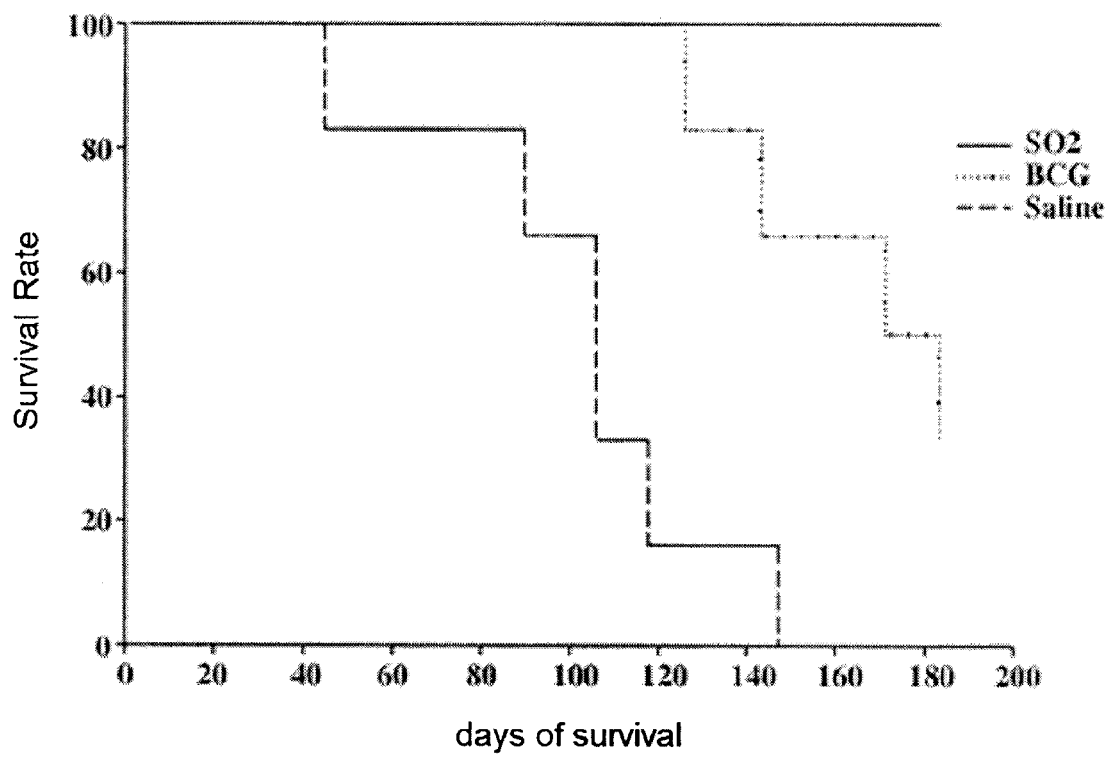

The guinea pigs that received the high dose were sacrificed 180 days after application or when a loss of 20% of the body weight was noted. The protection levels were determined by comparing the survival times of the guinea pigs of each treatment group. The progression of development of the lesions was also studied in the vaccinated/infected guinea pigs and compared with that observed in the unvaccinated/uninfected animals. During the phase of the experiment subsequent to inhalation, all the unvaccinated guinea pigs and four of the guinea pigs vaccinated with BCG were sacrificed at the human end point, before the time end point (180 days) due to severe and progressive disease (FIG. 6a). In contrast, all of the guinea pigs vaccinated with the SO2 strain of the present invention survived throughout the duration of the study. The guinea pigs vaccinated with the SO2 strain of the present invention survived significantly longer than those vaccinated with BCG ($p=0.018$), which, in turn, survived significantly longer than the control guinea pigs, which were treated with saline solution ($p=0.0049$). Furthermore, the guinea pigs vaccinated with the SO2 strain gained weight and did not present any visible or clinical sign of disease.

Figure 6B:
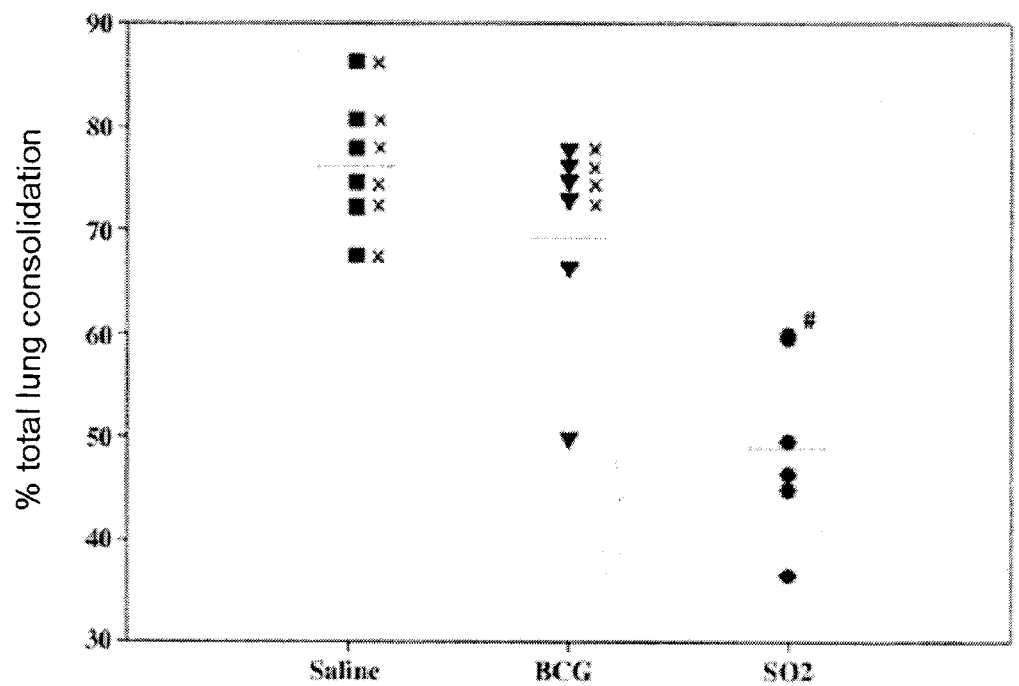
Figure 6C:
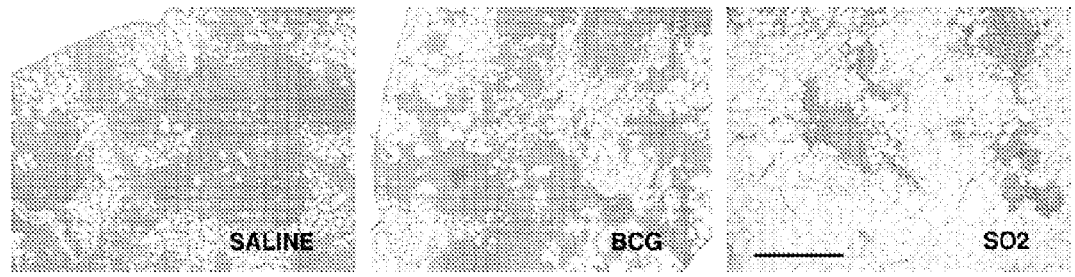
Figure 6D:
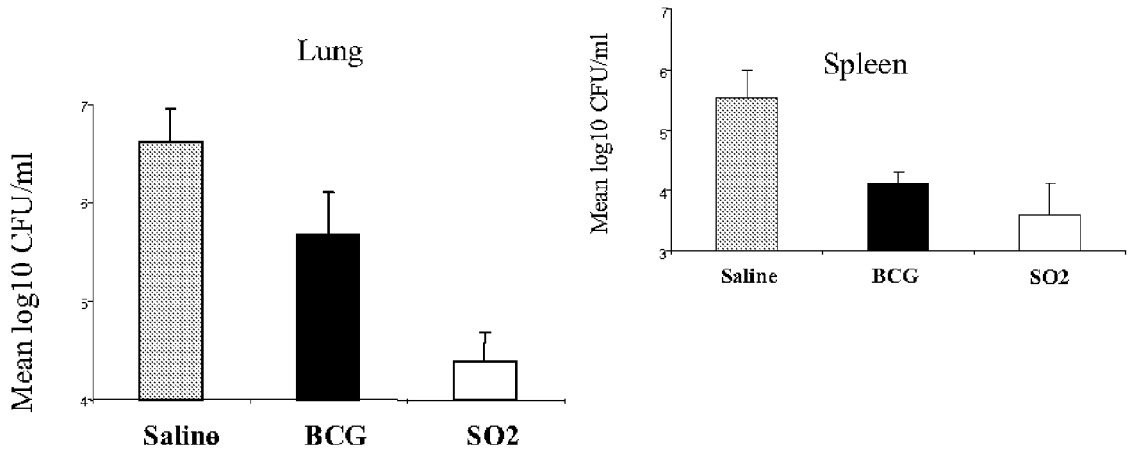

The extent of lung disease, measured by total lung consolidation, also varied between the different treatment groups. The highest level of progression of the disease was observed, as predicted, in the unvaccinated guinea pigs, and in this group of animals a mean percentage of consolidation of 76% was measured (FIG. 6b, 6c). Coalescence of granulomas was also pronounced in the guinea pigs vaccinated with BCG, with a mean consolidation of 70% measured in the lungs. In contrast, less consolidation (approximately 50%) was observed in the guinea pigs vaccinated with SO2 of the present invention, this consolidation being significantly less ($p<0.05$) than with the unvaccinated animals and those vaccinated with BCG (FIG. 6c). This reduction in the severity of the disease was also reflected in the bacterial counts of lung and spleen homogenates. In the vaccinated groups a difference in the levels of inhibition of *M. tuberculosis* H37Rv growth was observed in both organs. The numbers of CFUs recovered from guinea pigs vaccinated with SO2 were reduced by more than $1 \times \log_{in}$ compared to those of guinea pigs vaccinated with BCG, and this reduction was statistically significant ($p<0.05$) in the spleen (FIG. 6d). These data show that the SO2 strain of the present invention was better than BCG at conferring a higher survival rate on infected guinea pigs, reducing the severity of the disease in the lungs and preventing the infection from spreading to the spleen.

Example 7

Figure 7A:
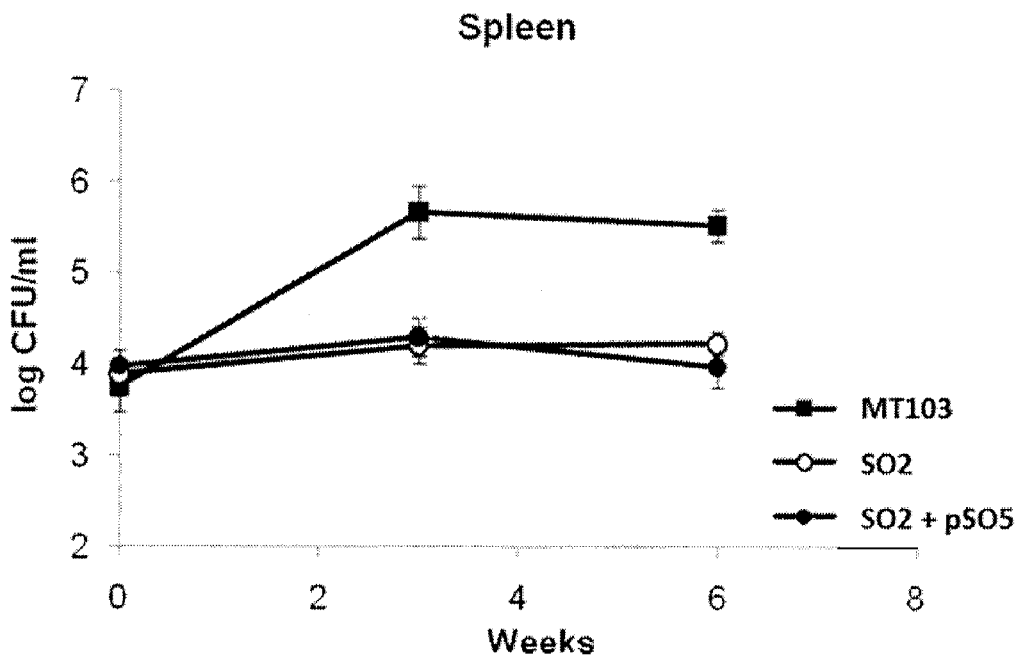
Figure 7B:
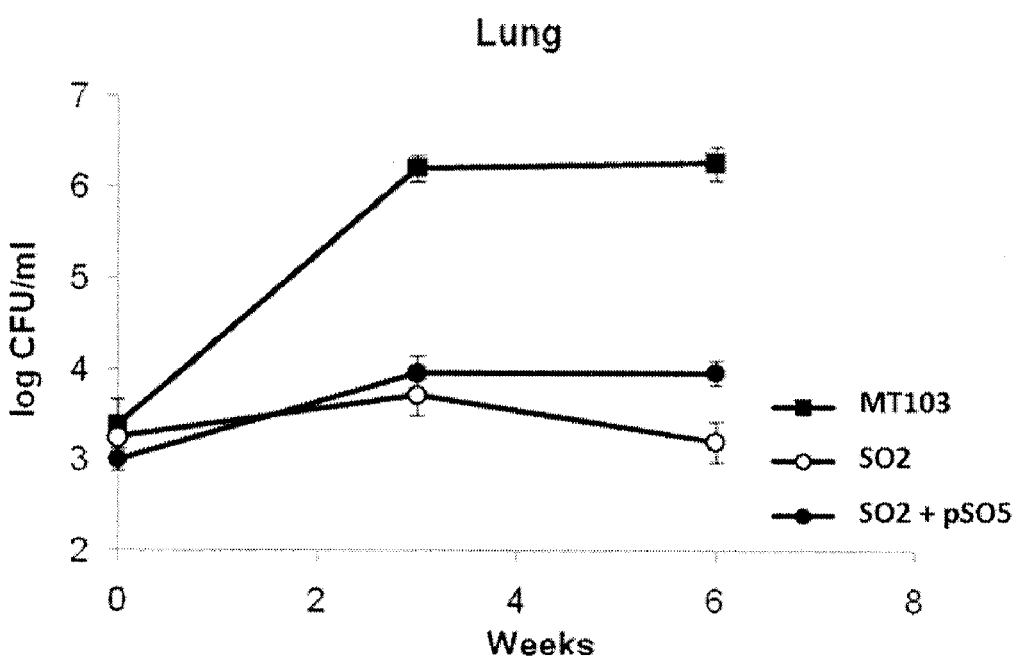
Figure 9:
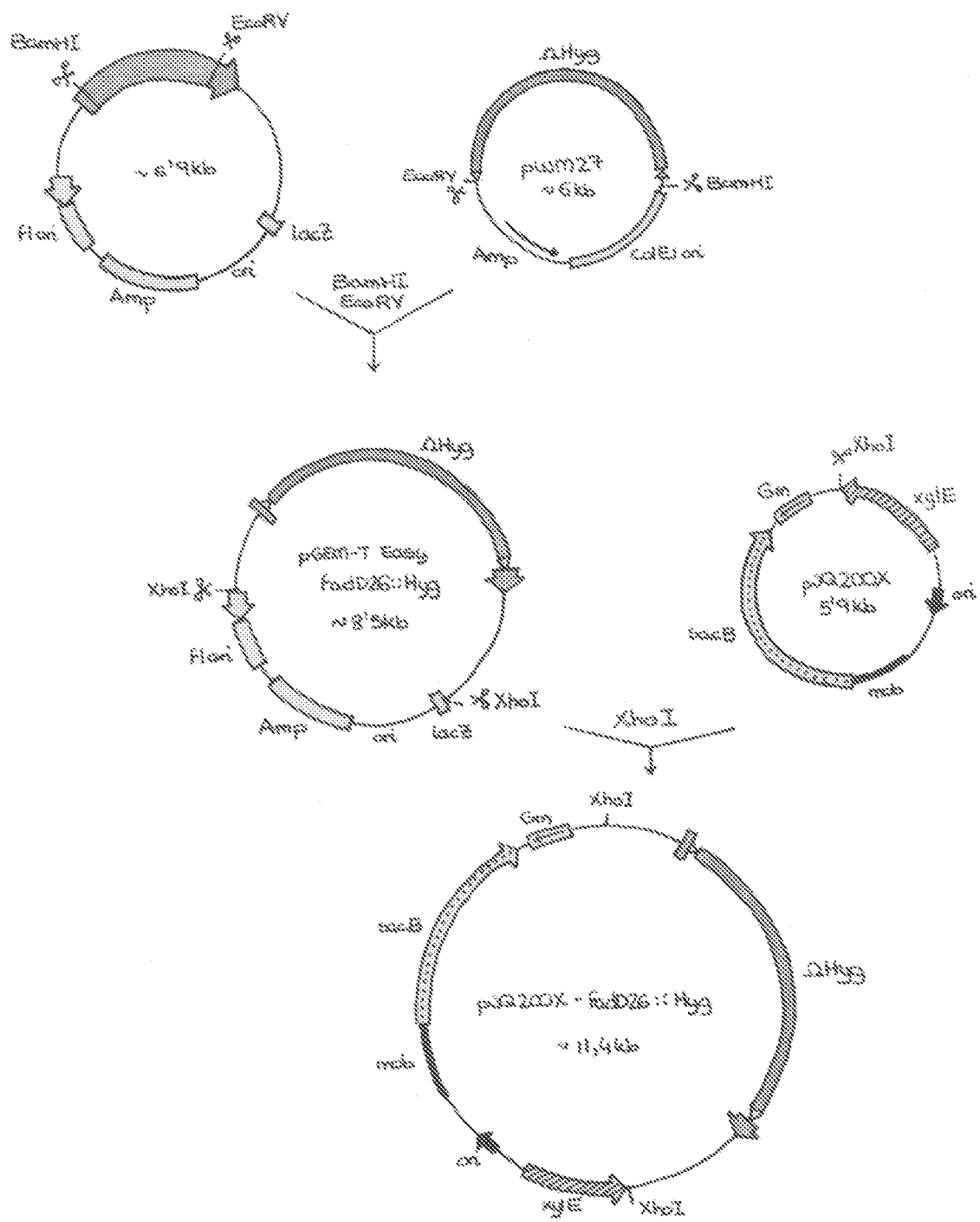
Figure 10:
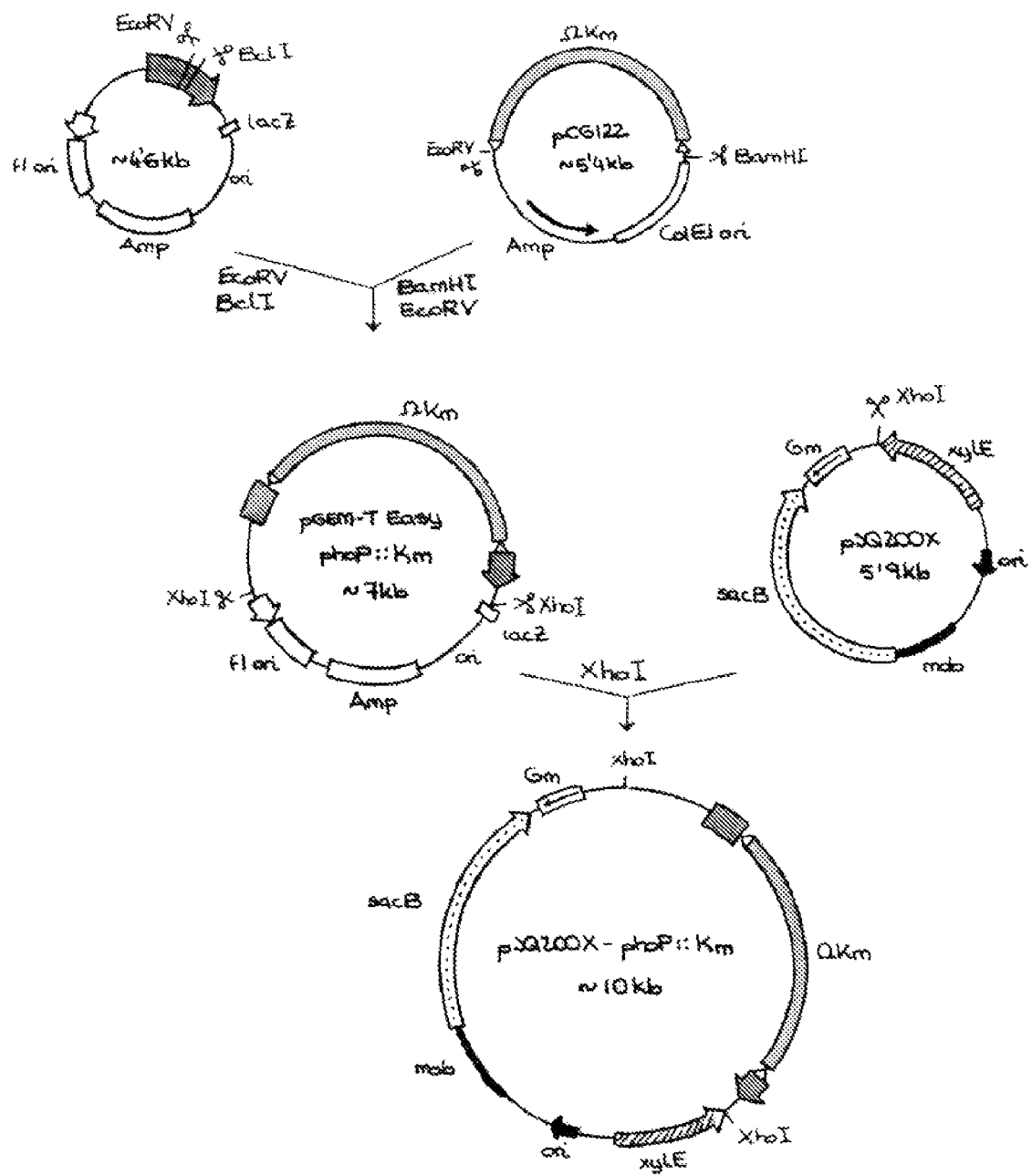

Attenuation of SO2 of the Present Invention is Due to the PhoP–DIM– Double Mutation Infection studies in Balb/C mice by intravenous injection of the SO2 (phoP– DIM–) strain compared to the wild-type MT103 strain and the strain complemented with phoP (SO2+ pSO5) showed that the attenuation of infection with SO2 in BalbC mice by intravenous injection is not restored by complementation with phoP. The reduction of colonies (CFU) in both spleen (FIG. 7a) and lung (FIG. 7b), measured after 3 and 6 weeks, were not restored in the complemented strain, as it is not virulent in immunocompetent mice, these experiments suggesting that the surprising attenuation could be due to a second additional mutation (FIG. 7).

Lipid studies of different strains of *M. tuberculosis* by thin layer chromatography showed that the SO2 strain does not produce DIM and this is independent of the phoP mutation (FIG. 8).

To show that SO2 is not toxic, six guinea pigs were inoculated with 50 times the vaccine dose. The survival rate was 100% after the 6-month duration of the experiment. A weight gain was observed in all the animals over the 6 months, showing the non-toxicity of the SO2 strain (Y=weight in grams and week of infection. X=time in weeks) FIG. 12.

Sensitivity to antituberculosis drugs was also studied. The minimum inhibitory concentration (MIC) was determined for the antituberculosis drugs Ethambutol, Isoniazid, Rifampicin and Streptomycin against *M. tuberculosis* strains H37Rv, MT103 (wild type) as the control and the SO2 strain. The values (micrograms/ml) indicate that after inactivation of the phoP gene the SO2 candidate vaccine strain conserves its sensitivity to the most common drugs clinically used against tuberculosis.

|  | Ethambutol | Isoniazid | Rifampicin | Streptomycin |
|---|---|---|---|---|
| H37Rv | 2 | 0.5 | <0.004 | <0.5 |
| MT103 | 2 | 0.5 | <0.004 | <0.5 |
| SO2 | 2 | 0.25 | <0.004 | <0.5 |

Studies of attenuation in intratracheally inoculated BalbC mice showed that with the *M. tuberculosis* DIM– (1A29) strain 50% of the mice had survived after 20 weeks. All of the animals inoculated with SO2 (phoP– and DIM– mutant) surprisingly survived for the 20 weeks of the experiment (FIG. 11).

Example 8

Protection of SO2 of the Present Invention is Due to the PhoP–DIM– Double Mutation Protection was studied in guinea pigs vaccinated and infected by aerosol with *M. tuberculosis* H37Rv. Guinea pig survival after 300 days. After subcutaneous vaccination the animals are infected with a virulent strain of *M. tuberculosis* (H37Rv) at a high dose to study survival. After 60 days the 6 guinea pigs that had not been vaccinated had died, whilst the groups vaccinated with SO2, phoP– and BCG had survived. After 300 days of infection 3 guinea pigs vaccinated with BCG and phoP– had died, compared to only one of the group vaccinated with SO2, which indicates that the protection of the phoP mutant is similar to that of the current vaccine BCG, whereas vaccination with SO2, the phoP– and DIM– double mutant, protects better in the guinea pig model (FIG. 13).

These protection studies in guinea pigs lasted 400 days, but the 6 unvaccinated guinea pigs had died after 60 days. After 400 days of infection 3 guinea pigs from the group vaccinated with SO2 (FIG. 14*a*) survived, whereas just 1 guinea pig vaccinated with BCG (FIG. 14*a* and FIG. 14*b*) and phoP– (FIG. 14*b*) had survived, indicating again that the protection of the phoP mutant is similar to that of BCG, whilst vaccination with SO2, the phoP– and DIM double mutant, protects better after the 400 days of the experiment.

Example 9

Construction of the Candidate Tuberculosis Vaccine Based on Mutation by Deletion of the fadD26 Gene The *M. tuberculosis* strains used for the construction of the mutant by deletion of the fadD26 (ΔfadD26) gene are SO2, which contains the phoP gene inactivated by insertion of a kanamycin resistance cassette, and the MT103 clinical strain.
1. Construction of the Plasmids
    1.1. Cloning of the fadD26 gene, which is involved in DIM synthesis. The fadD26 gene was amplified by PCR, using genomic DNA from *M. tuberculosis* H37Rv and using primers fadD26Fw (SEQ ID NO:1) and fadD26Rv (SEQ ID NO:2). The PCR product was inserted into the pGEM-T Easy vector (Promega) to construct plasmid pAZ1.
    1.2. Deletion of the fadD26 gene and insertion of the hygromycin resistance cassette. A BamHI-EcoRV fragment of pWM27 (Malaga et al., FEMS Microbiology letters 219 (2003) 261-268), which contains the res-Ωhyg-res cassette (the res sites, recognised by γδ resolvase, will make it possible to eliminate the resistance marker in a second passage), was inserted between the BamHI-EcoRV sites of fadD26 in pAZ1 to construct pAZ3.
    1.3. Construction of the suicide vector for inactivation of the gene by homologous recombination. Plasmid pAZ3 was digested with XhoI, releasing the fadD26:Ωhyg insert, which was incorporated into the pJQ200X vector, linearised with the same enzyme. The final plasmid was named pAZ5.
2. Construction of the *M. tuberculosis* DIM– Strains
    2.1. Plasmid pAZ5 was inserted into the *M. tuberculosis* SO2 and MT103 strains.
    2.2. Selection of the single recombinants. Culture in hygromycin (20 μg/ml) of the bacteria that include the plasmid and checking for its resistance to gentamicin (10 μg/ml).
    2.3. Selection of the double recombinants. Culture of the single recombinants in sucrose 2% (Pelicic et al. 1997) and hygromycin and checking for their sensitivity to gentamicin.
3. Elimination of the Antibiotic Resistance Marker from the ΔfadD26 Mutation.
    3.1. To eliminate the res-Ωhyg-res cassette and produce the mutation without an antibiotic resistance marker, plasmid pWM19, which contains γδ resolvase, is inserted and selected by gentamicin resistance. Then the plasmid is eliminated by incubating at 39° C. in sucrose 2% (Malaga et al. 2003).
Example 2.2.—The *M. tuberculosis* strain used for the construction of the double mutant by deletion ΔphoP ΔfadD26 is MT103 ΔfadD26.
4. Construction of the Plasmids
    4.1. Cloning of the phoP gene. The phoP gene was amplified by PCR, using genomic DNA from *M. tuberculosis* H37Rv and using primers phoPF (SEQ ID NO:3) and phoPR (SEQ ID NO:4). The PCR product was inserted into the pGEM-T Easy vector (Promega) to construct plasmid pAZ11.
    4.2. Deletion of the phoP gene and insertion of the kanamycin resistance cassette. A BamHI-EcoRV fragment of pCG122 (Malaga et al. 2003), which contains the res-Ωkm-res cassette, was inserted between the BclI-EcoRV sites of phoP in pAZ11 to construct pAZ13.
    4.3. Construction of the suicide vector for inactivation of the gene by homologous recombination. Plasmid pAZ13 was digested with XhoI, releasing the phoP::Ωkm insert, which was incorporated into the pJQ200X vector, linearised with the same enzyme. The final plasmid was named pAZ15.
5. Construction of the *M. tuberculosis* ΔphoP ΔfadD26 Double Mutant Strain.
    5.1 Plasmid pAZ15 will be inserted into the *M. tuberculosis* MT103 ΔfadD26 strain.
    5.2. Selection of the single recombinants. Culture in kanamycin (20 μg/ml) of the bacteria that include the plasmid and checking for its resistance to gentamicin (10 μg/ml).

5.3. Selection of the double recombinants. Culture of the single recombinants in sucrose 2% (Pelicic et al. 1997) and kanamycin and checking for their sensitivity to gentamicin.

6. Elimination of the Antibiotic Resistance Marker from the ΔphoP Mutation.

6.1. To eliminate the res-Ωkm-res cassette and produce the mutation without an antibiotic resistance marker, plasmid pWM19, which contains γδ resolvase, will be inserted and selected by hygromycin resistance (20 μg/ml). Then the plasmid will be eliminated by incubating at 39° C. in sucrose 2% (Malaga et al. 2003).

REFERENCES

1 WHO. Global Report tuberculosis. Global tuberculosis control—surveillance, planning, financining. World Health Organization, Geneva, 2005. www.who.int/tb/publications/global_report/en/index.
2 WHO/IUATLD. Anti-Tuberculosis Drug Resistance in the World. Report no. 3: prevalence and trends. WHO/IUATLD. Global Project on Anti-Tuberculosis Drug Resistance Surveillance 1999-2002. World Health Organization and International Union Against Tuberculosis and Lung Disease, Geneva, 2004. www.who.int/tb/publications/who_htm_tb_2004_343/en/index.
3 Young, D. B. Building a better tuberculosis vaccine. Nat Med 2003, 9(5), 503-504.
4 Fine, P.E. Variation in protection by BCG: implications of and for heterologous immunity. Lancet 1995, 346(8986), 1339-1345.
5 Behr, M. A. BCG—different strains, different vaccines? Lancet Infect Dis 2002, 2(2), 86-92.
6 Pym, A. S., Brodin, P., Majlessi, L. et al. Recombinant BCG exporting ESAT-6 confers enhanced protection against tuberculosis. Nat Med 2003, 9(5), 533-539.
7 Young, D. B. Current tuberculosis vaccine development. Clin Infect Dis 2000, 30 Suppl 3, S254-256.
8 Orme, I. M. Preclinical testing of new vaccines for tuberculosis: A comprehensive review. Vaccine 2006, 24(1), 2-19.
9 Kaufmann, S. H. Is the development of a new tuberculosis vaccine possible? Nat Med 2000, 6(9), 955-960.
10 Britton, W. J. & Palendira, U. Improving vaccines against tuberculosis. Immunol Cell Biol 2003, 81(1), 34-45.
11 Pelicic, V., Jackson, M., Reyrat, J. M., Jacobs, W. R., Jr., Gicquel, B. & Guilhot, C. Efficient allelic exchange and transposon mutagenesis in Mycobacterium tuberculosis. Proc Natl Acad Sci USA 1997, 94(20), 10955-10960.
12 Bardarov, S., Kriakov, J., Carriere, C. et al. Conditionally replicating mycobacteriophages: a system for transposon delivery to Mycobacterium tuberculosis. Proc Natl Acad Sci USA 1997, 94(20), 10961-10966.
13 Clark-Curtiss, J. E. & Haydel, S. E. Molecular genetics of Mycobacterium tuberculosis pathogenesis. Annu Rev Microbiol 2003, 57, 517-549.
14 Cole, S. T., Brosch, R., Parkhill, J. et al. Deciphering the biology of Mycobacterium tuberculosis from the complete genome sequence. Nature 1998, 393(6685), 537-544.
15 Camacho, L. R., Ensergueix, D., Perez, E., Gicquel, B. & Guilhot, C. Identification of a virulence gene cluster of Mycobacterium tuberculosis by signature-tagged transposon mutagenesis. Mol Microbiol 1999, 34(2), 257-267.
16 Cox, J. S., Chen, B., McNeil, M. & Jacobs, W. R., Jr. Complex lipid determines tissue-specific replication of Mycobacterium tuberculosis in mice. Nature 1999, 402(6757), 79-83.
17 Sambandamurthy, V. K., Wang, X., Chen, B. et al. A pantothenate auxotroph of Mycobacterium tuberculosis is highly attenuated and protects mice against tuberculosis. Nat Med 2002, 8(10), 1171-1174.
18 Smith, D. A., Parish, T., Stoker, N. G. & Bancroft, G. J. Characterization of auxotrophic mutants of Mycobacterium tuberculosis and their potential as vaccine candidates. Infect Immun 2001, 69(2), 1142-1150.
19 Groisman, E. A. The pleiotropic two-component regulatory system PhoP–PhoQ. J Bacteriol 2001, 183(6), 1835-1842.
20 Fields, P. I., Groisman, E. A. & Heffron, F. A Salmonella locus that controls resistance to microbicidal proteins from phagocytic cells. Science 1989, 243(4894 Pt 1), 1059-1062.
21 Soto, C. Y., Menendez, M. C., Perez, E. et al. IS6110 mediates increased transcription of the phoP virulence gene in a multidrug-resistant clinical isolate responsible for tuberculosis outbreaks. J Clin Microbiol 2004, 42(1), 212-219.
22 Gonzalo Asensio, J., Maia, C., Ferrer, N. L. et al. The virulence-associated two-component PhoP–PhoR system controls the biosynthesis of polyketide-derived lipids in Mycobacterium tuberculosis. J Biol Chem 2005.
23 Perez, E., Samper, S., Bordas, Y., Guilhot, C., Gicquel, B. & Martin, C. An essential role for phoP in Mycobacterium tuberculosis virulence. Mol Microbiol 2001, 41(1), 179-187.
24 Pym, A. S., Brodin, P., Brosch, R., Huerre, M. & Cole, S. T. Loss of RD1 contributed to the attenuation of the live tuberculosis vaccines Mycobacterium bovis BCG and Mycobacterium microti. Mol Microbiol 2002, 46(3), 709-717.
25 Sambrook, J. a. R., D W. Molecular Cloning a laboratory manual, Cold Spring Harbor Laboratory Press, New York, 2001.
26 Arriaga, A. K., Orozco, E. H., Aguilar, L. D., Rook, G. A. & Hernandez Pando, R. Immunological and pathological comparative analysis between experimental latent tuberculous infection and progressive pulmonary tuberculosis. Clin Exp Immunol 2002, 128(2), 229-237.
27 Williams, A., Davies, A., Marsh, P. D., Chambers, M. A. & Hewinson, R. G. Comparison of the protective efficacy of bacille calmette-Guerin vaccination against aerosol challenge with Mycobacterium tuberculosis and Mycobacterium bovis. Clin Infect Dis 2000, 30 Suppl 3, S299-301.
28 Hondalus, M. K., Bardarov, S., Russell, R., Chan, J., Jacobs, W. R., Jr. & Bloom, B. R. Attenuation of and protection induced by a leucine auxotroph of Mycobacterium tuberculosis. Infect Immun 2000, 68(5), 2888-2898.
29 Horwitz, M. A., Lee, B. W., Dillon, B. J. & Harth, G. Protective immunity against tuberculosis induced by vaccination with major extracellular proteins of Mycobacterium tuberculosis. Proc Natl Acad Sci USA 1995, 92(5), 1530-1534.
30 Baldwin, S. L., D'Souza, C., Roberts, A. D. et al. Evaluation of new vaccines in the mouse and guinea pig model of tuberculosis. Infect Immun 1998, 66(6), 2951-2959.
31 Horwitz, M. A., Harth, G., Dillon, B. J. & Maslesa-Galic, S. Recombinant bacillus calmette-guerin (BCG) vaccines expressing the Mycobacterium tuberculosis 30-kDa major secretory protein induce greater protective immunity against tuberculosis than conventional BCG vaccines in a highly susceptible animal model. Proc Natl Acad Sci USA 2000, 97(25), 13853-13858.

32 Behr, M. A., Wilson, M. A., Gill, W. P. et al. Comparative genomics of BCG vaccines by whole-genome DNA microarray. Science 1999, 284(5419), 1520-1523.

33 Mollenkopf, H. J., Kursar, M. & Kaufmann, S. H. Immune Response to Postprimary Tuberculosis in Mice: *Mycobacterium tuberculosis* and *Mycobacterium bovis* bacille Calmette-Guerin Induce Equal Protection. *J Infect Dis* 2004, 190(3), 588-597.

34 Sampson, S. L., Dascher, C. C., Sambandamurthy, V. K. et al. Protection elicited by a double leucine and pantothenate auxotroph of *Mycobacterium tuberculosis* in guinea pigs. *Infect Immun* 2004, 72(5), 3031-3037.

35 Horwitz, M. A. & Harth, G. A new vaccine against tuberculosis affords greater survival after challenge than the current vaccine in the guinea pig model of pulmonary tuberculosis. *Infect Immun* 2003, 71(4), 1672-1679.

36 Brandt, L., Skeiky, Y. A., Alderson, M. R. et al. The protective effect of the *Mycobacterium bovis* BCG vaccine is increased by coadministration with the *Mycobacterium tuberculosis* 72-kilodalton fusion polyprotein Mtb72F in *M. tuberculosis*-infected guinea pigs. *Infect Immun* 2004, 72(11), 6622-6632.

37 Wiegeshaus, E. H., McMurray, D. N., Grover, A. A., Harding, G. E. & Smith, D. W. Host-parasite relationships in experimental airborne tuberculosis. 3. Relevance of microbial enumeration to acquired resistance in guinea pigs. *Am Rev Respir Dis* 1970, 102(3), 422-429.

38 Williams, A., Hatch, G. J., Clark, S. O. et al. Evaluation of vaccines in the EU TB Vaccine Cluster using a guinea pig aerosol infection model of tuberculosis. *Tuberculosis (Edinb)* 2005, 85(1-2), 29-38.

39 McShane, H., Pathan, A. A., Sander, C. R. et al. Recombinant modified vaccinia virus Ankara expressing antigen 85A boosts BCG-primed and naturally acquired antimycobacterial immunity in humans. *Nat Med* 2004, 10(11), 1240-1244.

40 Kamath, A. T., Fruth, U., Brennan, M. J. et al. New live mycobacterial vaccines: the Geneva consensus on essential steps towards clinical development. *Vaccine* 2005, 23(29), 3753-3761.

The invention claimed is:

1. An isolated microorganism belonging to the *Mycobacterium tuberculosis* complex, wherein in said microorganism,
   a) the phoP gene is inactivated or deleted; and
   b) a second gene is inactivated or deleted to prevent DIM production.

2. The isolated microorganism of 1, wherein DIM production is inactivated through the deletion or inactivation of the fadD26 gene.

3. The isolated microorganism of claim 1, wherein said second gene is fadD26.

4. The isolated microorganism of claim 1, wherein the microorganism is *Mycobacterium tuberculosis*.

5. The isolated microorganism of claim 4, wherein the second gene is Rv2930 (fadD26) and the phoP gene is Rv0757.

6. A process for constructing an isolated microorganism according to claim 1, comprising the steps of:
   a) inactivating or deleting the phoP gene; and
   b) inactivating or deleting a second gene to prevent DIM production.

7. The process of claim 6, wherein the phoP gene is inactivated by inactivating the phoP gene.

8. The process of claim 6, wherein DIM production is inactivated by deleting or inactivating the fadD26 gene.

9. A pharmaceutical formulation comprising an isolated microorganism belonging to the *Mycobacterium tuberculosis* complex and at least one pharmacologically suitable excipient, wherein in said microorganism
   a) the phoP gene is inactivated or deleted; and
   b) a second gene is inactivated or deleted to prevent DIM production.

10. A method of vaccinating a human or animal, said method comprising the steps of administering to a patient an effective amount of a pharmaceutical formulation according to claim 9.

11. A method of treating or preventing tuberculosis in a human or animal, said method comprising the step of administering to a patient an effective amount of pharmaceutical formulation according to claim 9.

12. A method for enhancing an immune response in a subject to an immunogen comprising administering the pharmaceutical formulation of claim 9 in conjunction with an immunogen to a subject thereby enhancing the subject's immune response to the immunogen.

13. A process for preparing a vaccine for immunising against or preventing the symptoms caused by tuberculosis, comprising the steps of:
   a) incorporating an isolated microorganism according to claim 1 into a suitable medium for administration in humans or animals in a therapeutically effective dose, wherein in said microorganism
      (i) the phoP gene is inactivated or deleted; and
      (ii) a second gene is inactivated or deleted to prevent DIM production; and
   b) optionally adding at least one excipient that is pharmacologically suitable for the production of vaccines.

14. The isolated microorganism of claim 1 suitable as an vector wherein said microorganism further comprises another immunogen.

* * * * *